United States Patent
Lee et al.

(10) Patent No.: US 10,568,536 B2
(45) Date of Patent: Feb. 25, 2020

(54) ELECTRONIC DEVICE AND CONTROLLING METHOD THEREOF

(71) Applicant: LG ELECTRONICS INC., Seoul (KR)

(72) Inventors: Younjae Lee, Seoul (KR); Hyoungkil Yoon, Seoul (KR); Kihyuk Lee, Seoul (KR); Eunhwa Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 207 days.

(21) Appl. No.: 15/642,110

(22) Filed: Jul. 5, 2017

(65) Prior Publication Data

US 2018/0028094 A1     Feb. 1, 2018

(30) Foreign Application Priority Data

Jul. 29, 2016  (KR) .......................... 10-2016-0096675

(51) Int. Cl.
| | | |
|---|---|---|
| *G01G 19/44* | (2006.01) | |
| *A61B 5/053* | (2006.01) | |
| *G01G 19/50* | (2006.01) | |
| *G01G 23/37* | (2006.01) | |

(52) U.S. Cl.
CPC ........... *A61B 5/0537* (2013.01); *G01G 19/50* (2013.01); *G01G 23/3721* (2013.01)

(58) Field of Classification Search
None
See application file for complete search history.

(56) References Cited

U.S. PATENT DOCUMENTS

| | | |
|---|---|---|
| 5,611,351 A | 3/1997 | Sato et al. |
| 2005/0171451 A1 | 8/2005 | Yeo et al. |
| 2009/0088661 A1* | 4/2009 | Suzuki ................. A61B 5/0537 600/547 |
| 2010/0185990 A1* | 7/2010 | Ha ........................... G06F 3/01 715/863 |
| 2010/0210921 A1 | 8/2010 | Park et al. |
| 2013/0032413 A1* | 2/2013 | Smith ............................... 177/1 |
| 2014/0069729 A1* | 3/2014 | Shih ..................... G01G 19/445 177/144 |

FOREIGN PATENT DOCUMENTS

| | | |
|---|---|---|
| JP | 2003339671 | 12/2003 |
| WO | 2001050954 | 7/2001 |

OTHER PUBLICATIONS

PCT International Application No. PCT/KR2017/006775, Notification of Transmittal of the International Search Report and the Written Opinion of the International Searching Authority, or Declaration dated Sep. 18, 2017, 12 pages.

* cited by examiner

*Primary Examiner* — Etsub D Berhanu
*Assistant Examiner* — Jairo H Portillo
(74) *Attorney, Agent, or Firm* — Lee, Hong, Degerman, Kang & Waimey

(57) ABSTRACT

Disclosed are an electronic device and operating method thereof. The present invention includes recognizing an electrode initially in contact with the user's body part among a plurality of electrodes as a first pair, recognizing the rest of the electrodes contacted with the user's body as a second pair, measuring a current flowing between the recognized first and second pairs, determining a biometric information of the user based on the measured current and load, and outputting the determined biometric information.

11 Claims, 25 Drawing Sheets

FIG. 5
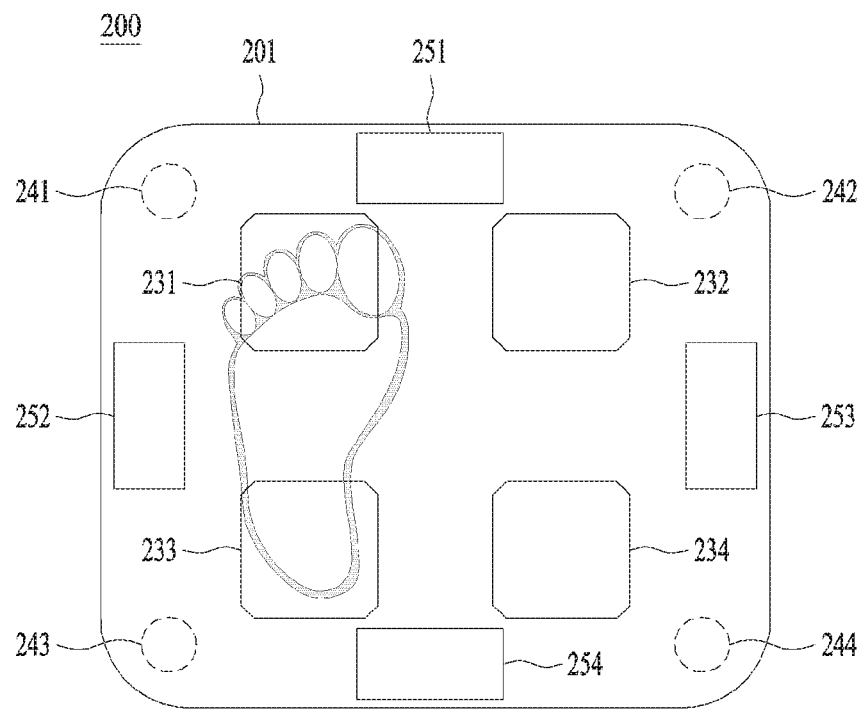
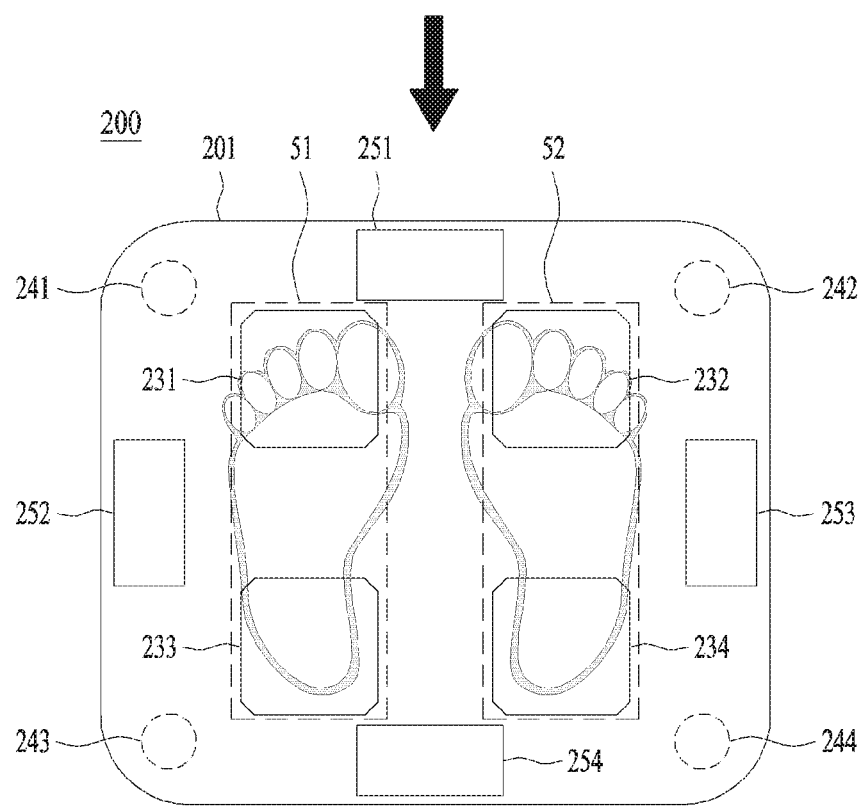

FIG. 6
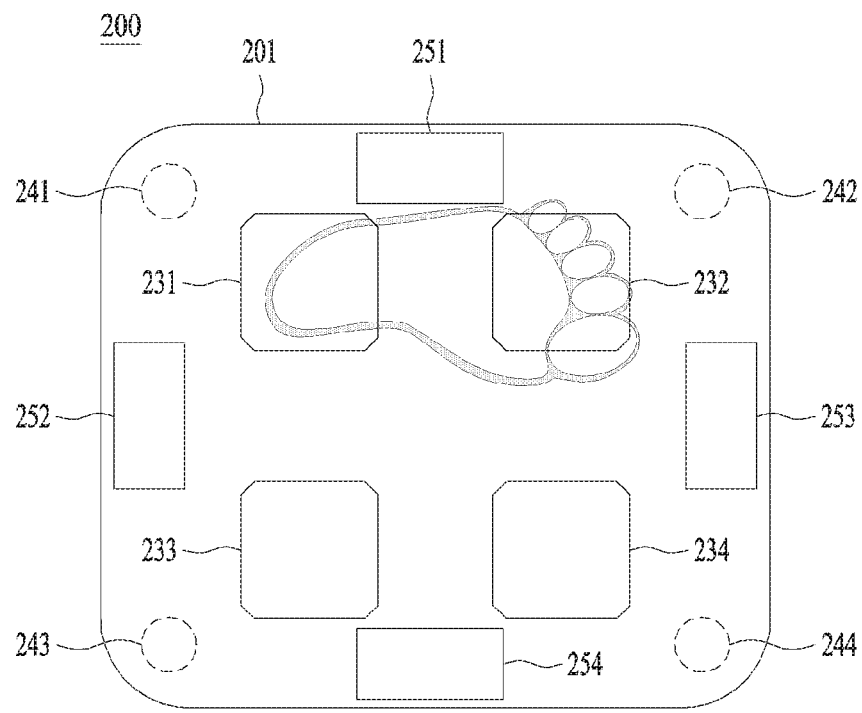
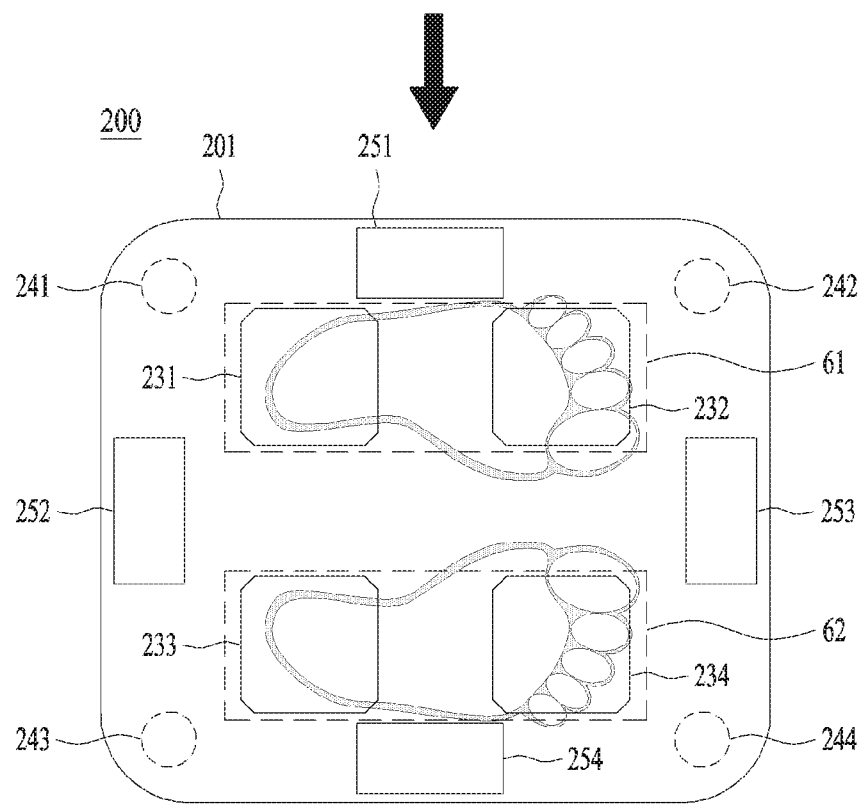

FIG. 7
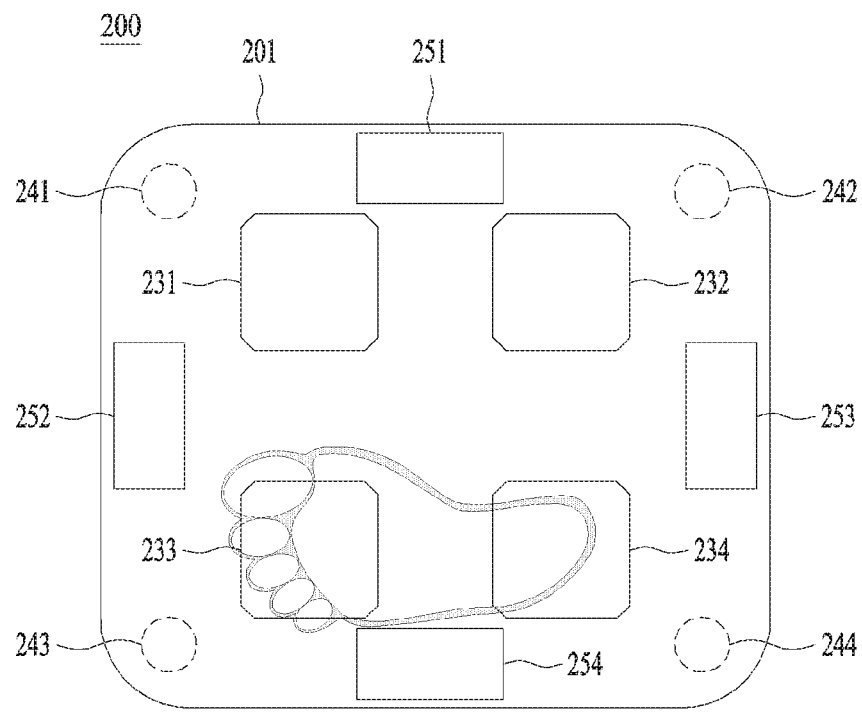
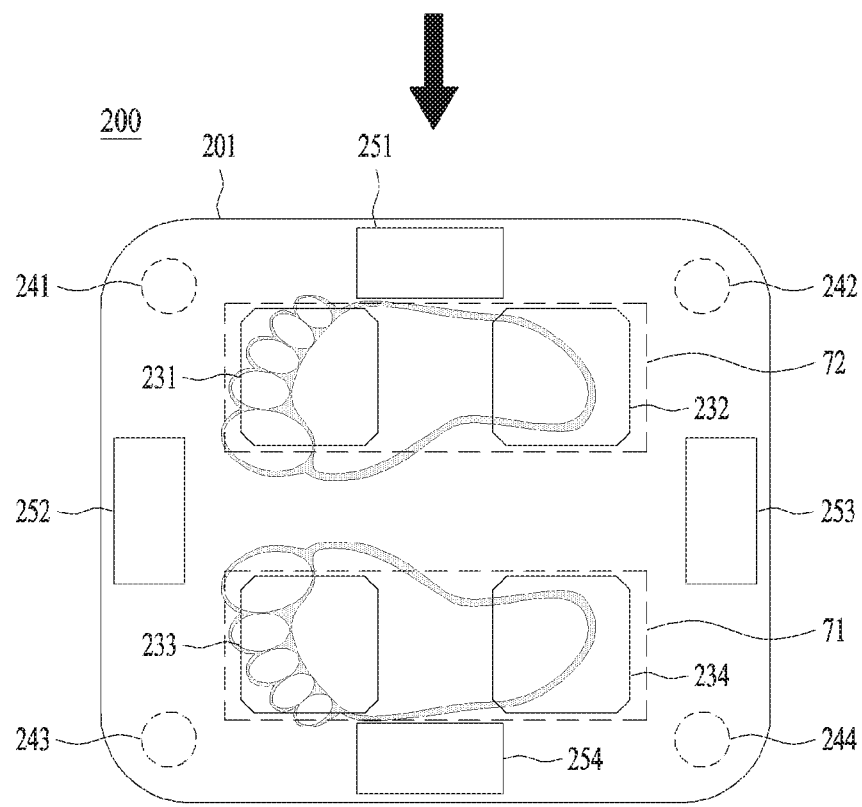

FIG. 8
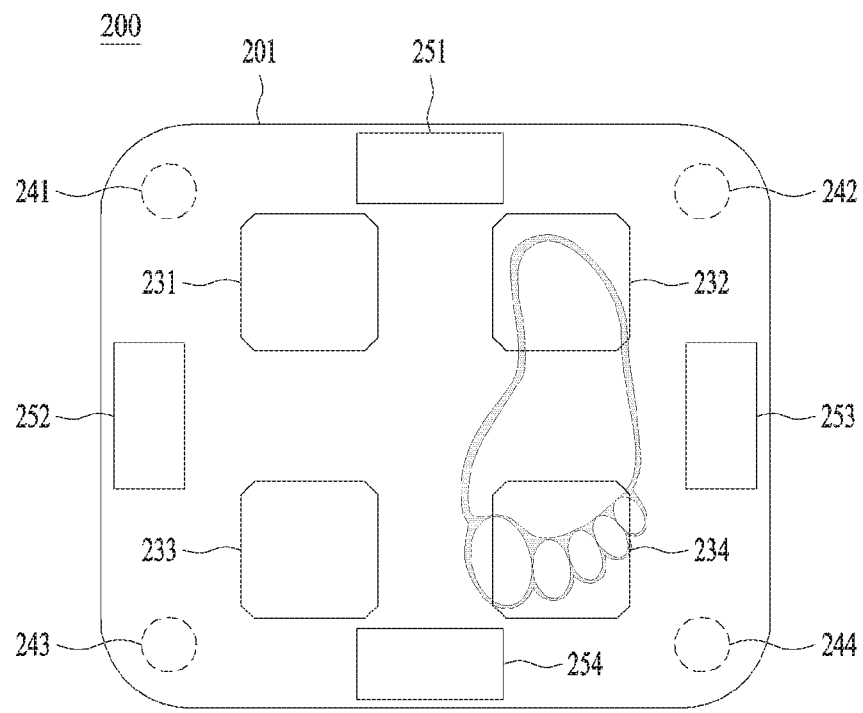
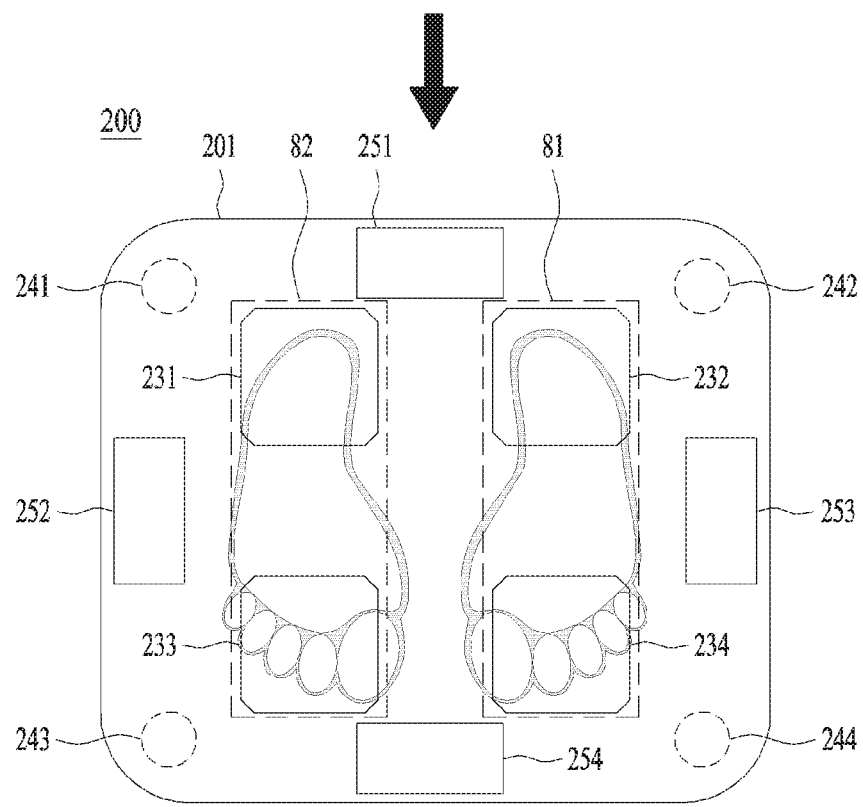

FIG. 11
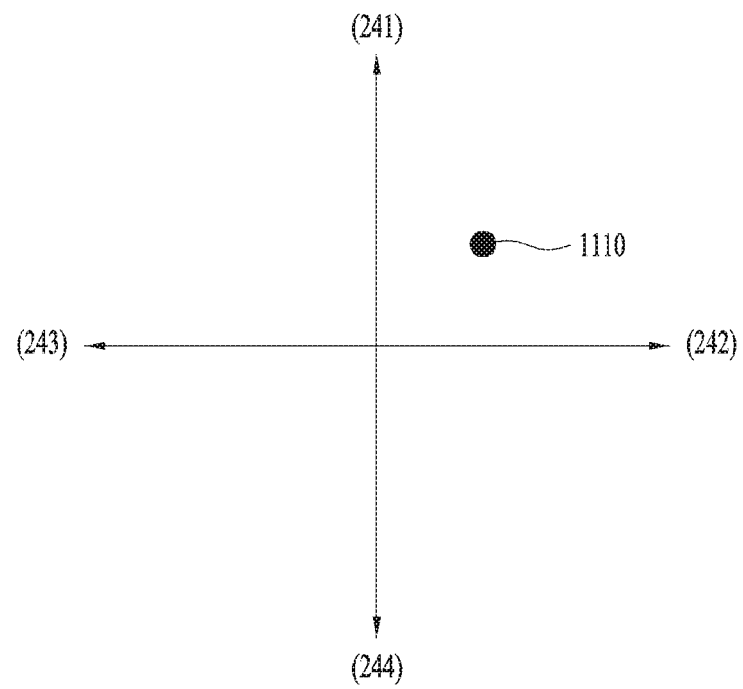
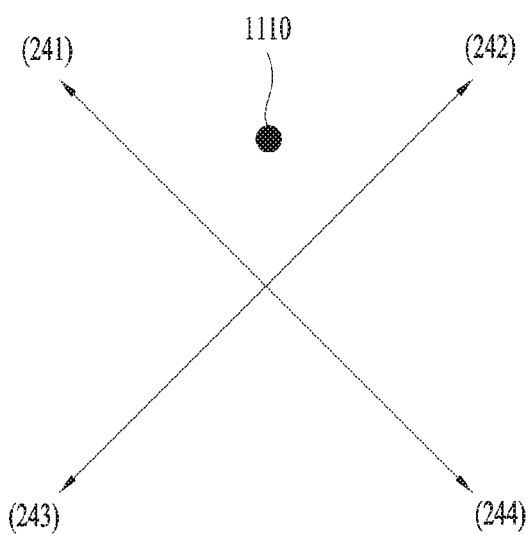

FIG. 14
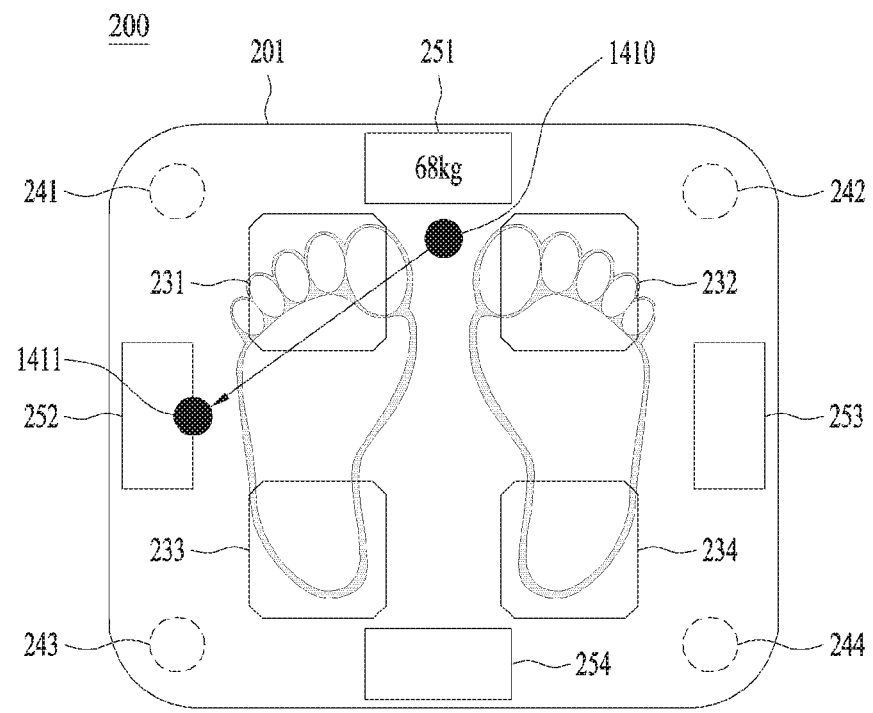
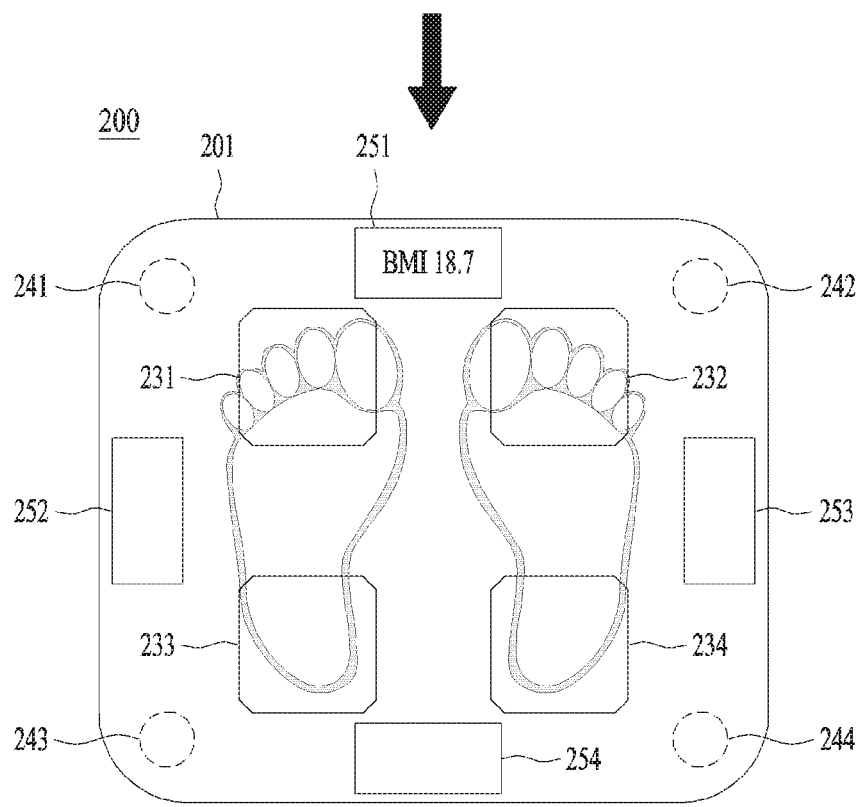

FIG. 15
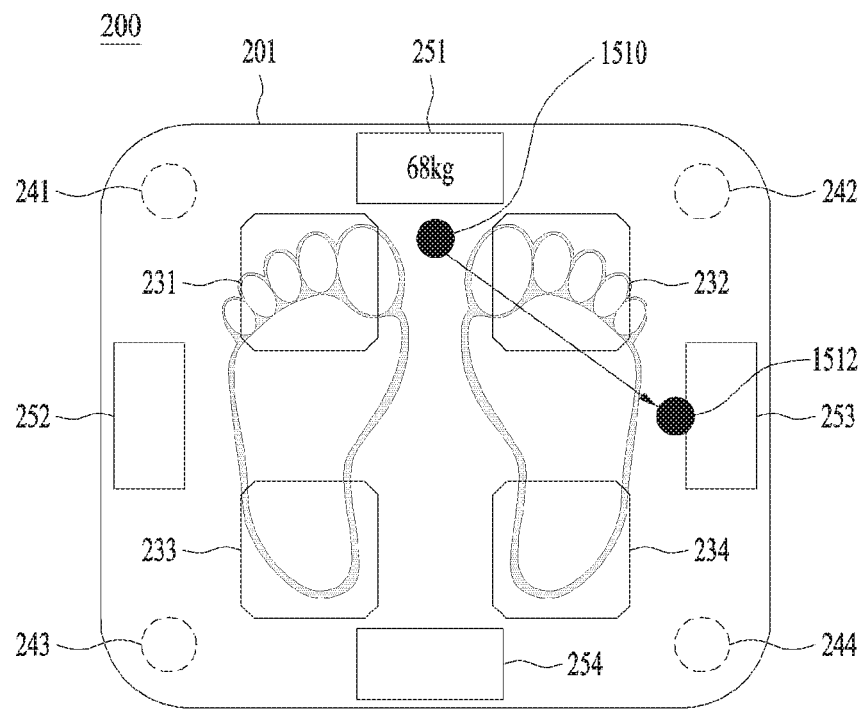
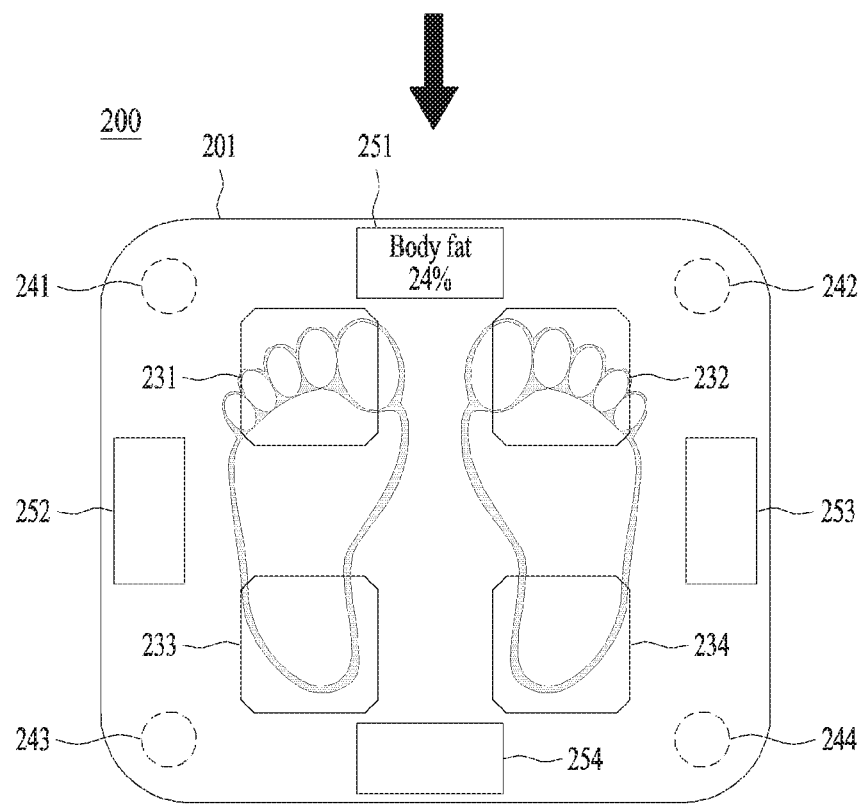

FIG. 16
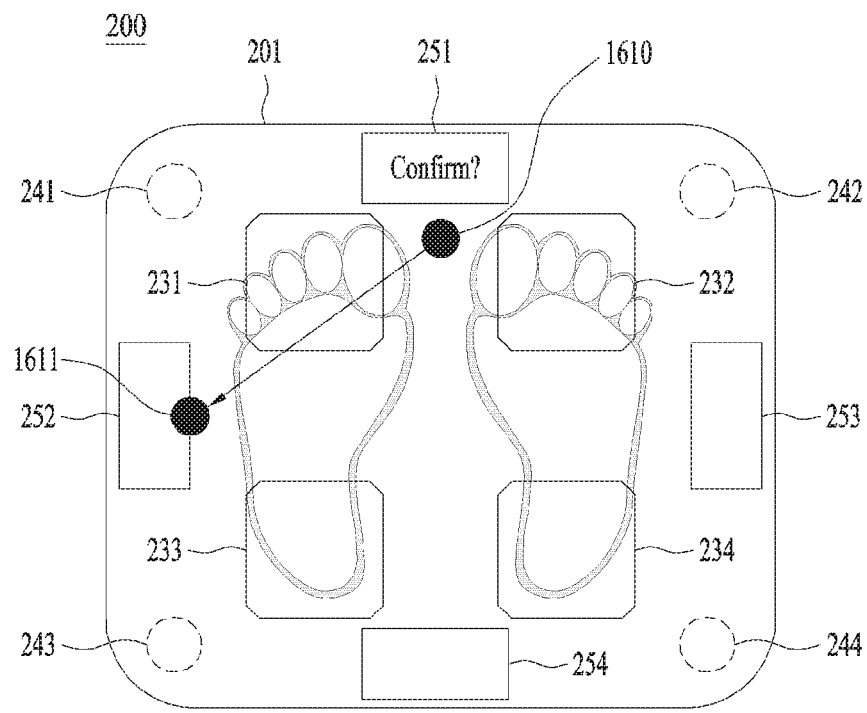
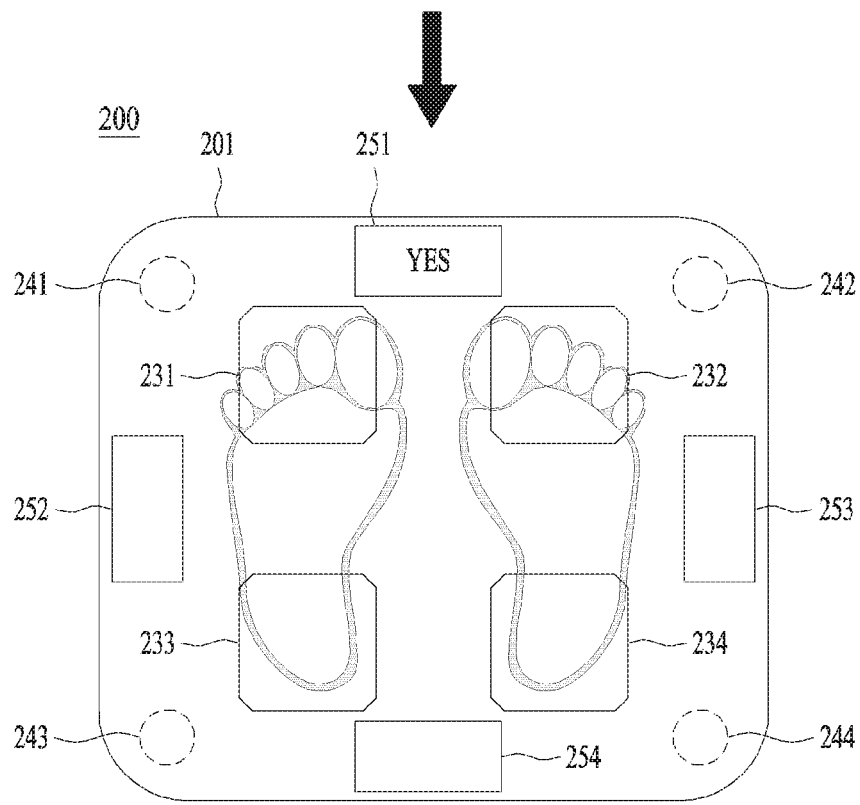

FIG. 17
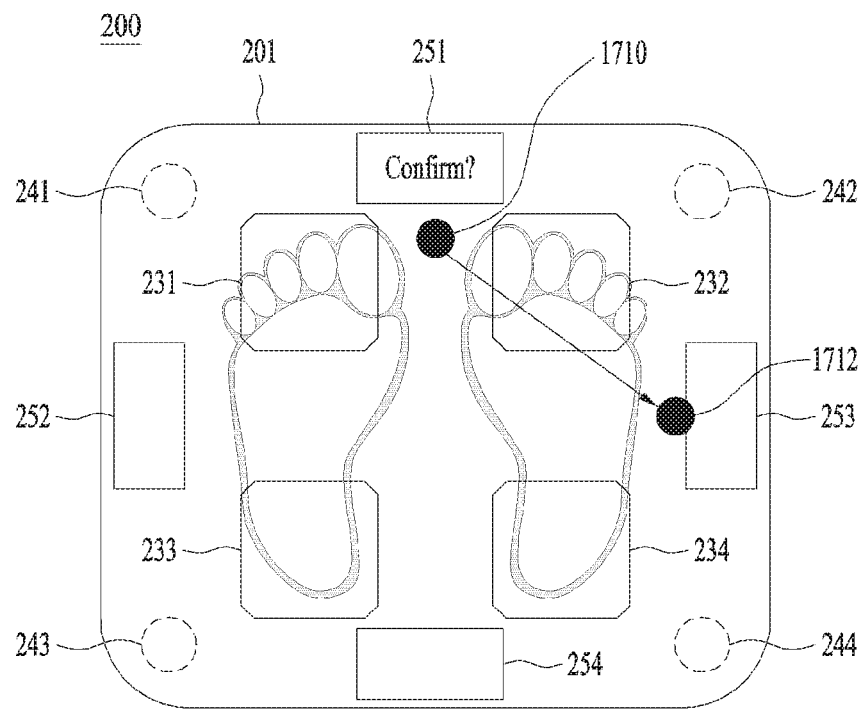
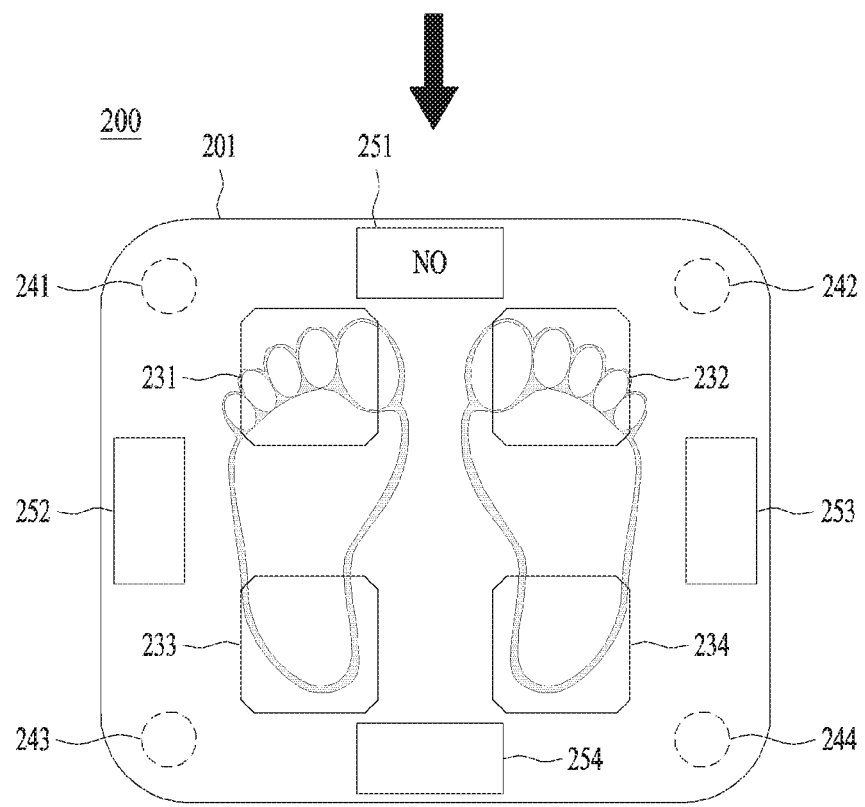

FIG. 18
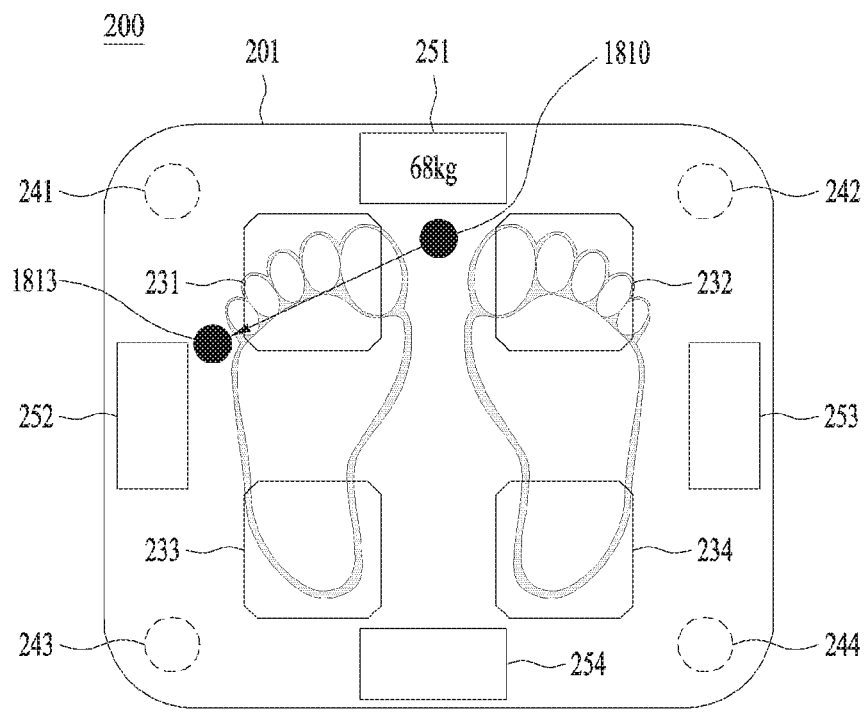
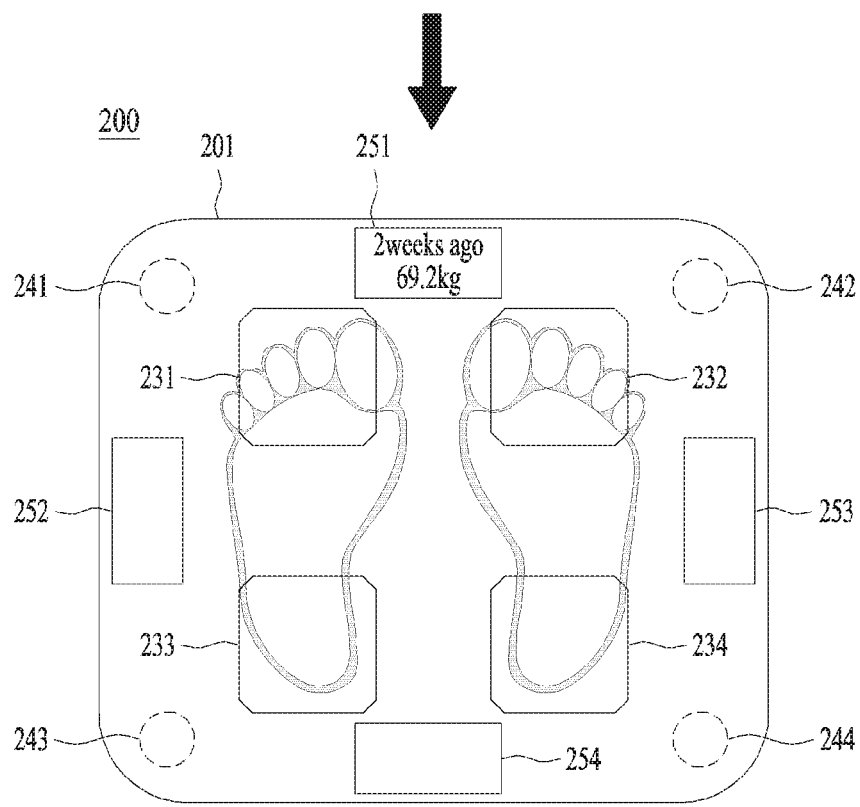

FIG. 19
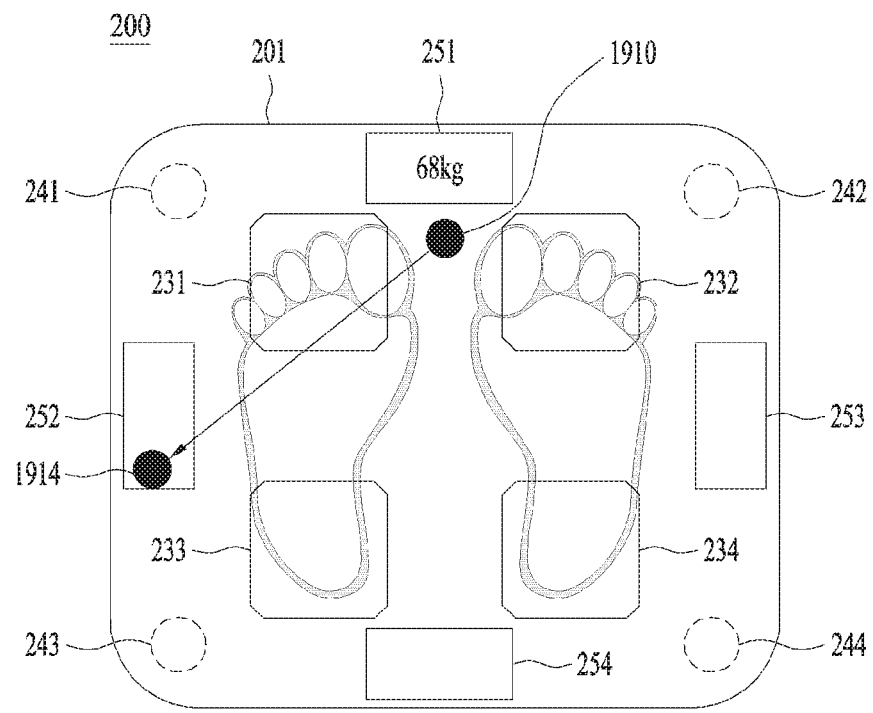
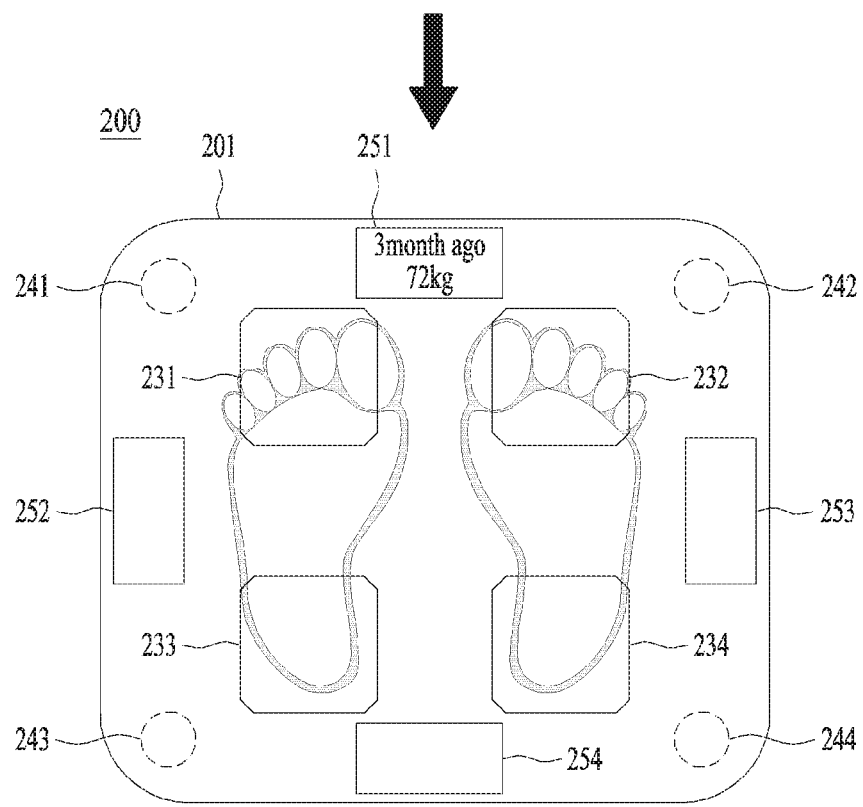

FIG. 20
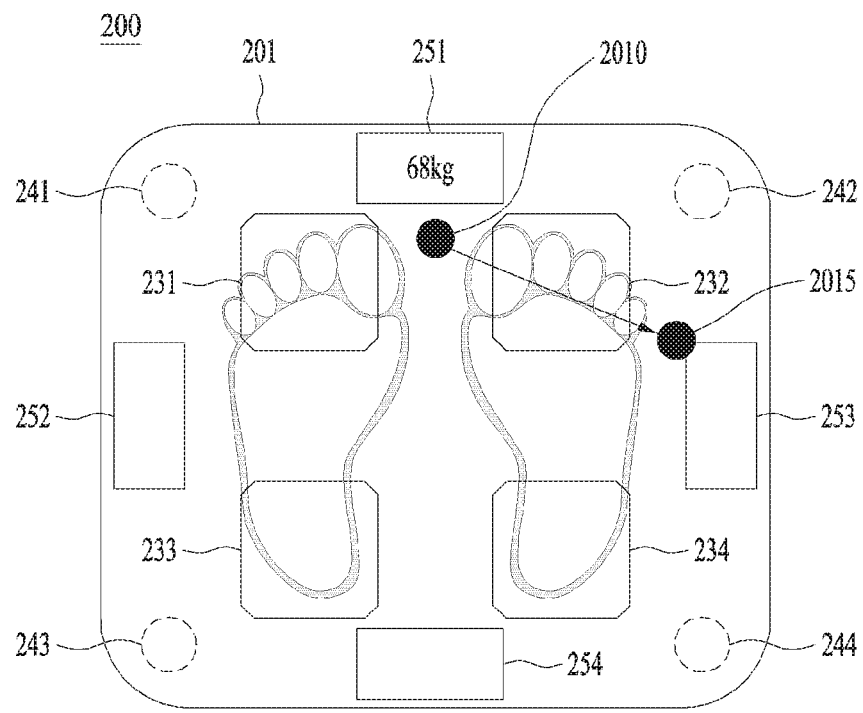
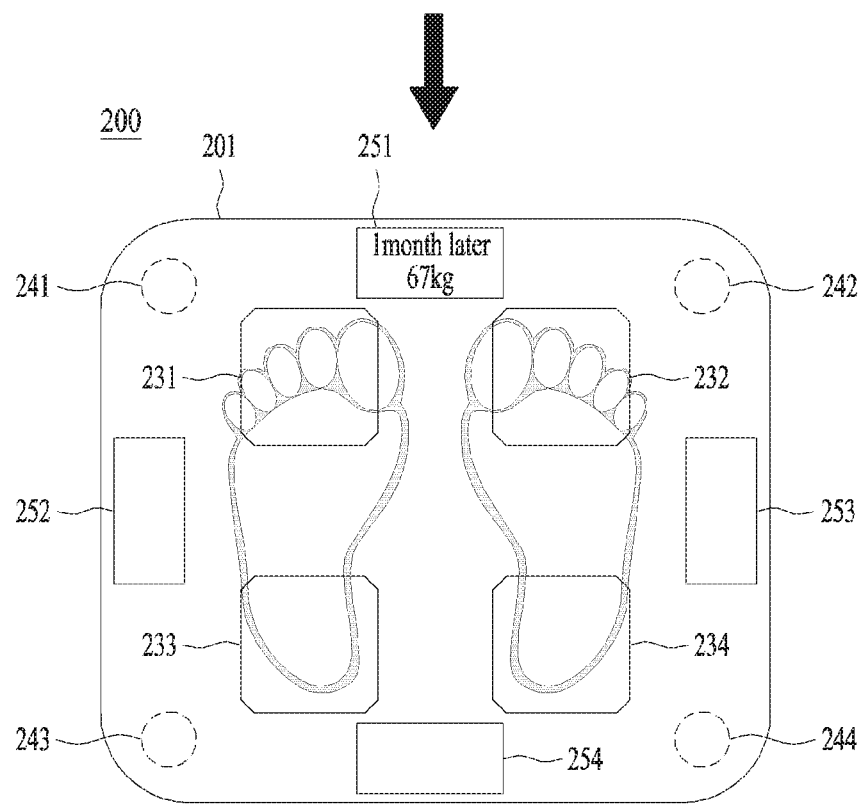

ELECTRONIC DEVICE AND CONTROLLING METHOD THEREOF

Pursuant to 35 U.S.C. § 119(a), this application claims the benefit of earlier filing date and right of priority to Korean Application No. 10-2016-0096675, filed on Jul. 29, 2016, the contents of which are all hereby incorporated by reference herein in its entirety.

BACKGROUND OF THE INVENTION

Field of the Invention

The present invention relates to an electronic device, and more particularly, to an electronic device and controlling method thereof. Although the present invention is suitable for a wide scope of applications, it is particularly suitable for measuring various biometric information.

Discussion of the Related Art

A healthcare device is a device capable of measuring various biometric informations related to health at a place (e.g., home, gym, office, etc.) that can be easily accessed by users. Such a healthcare device is devised to provide biometric information helpful to health management variously and accurately. And, wide-ranging products including a device for simply providing numerical values, a device for providing details based on the measured numerical values and the like have been released.

Recently, a healthcare device is combined with IoT (Internet of Things), thereby providing biometric information measured by the healthcare device to other devices of a user. Hence, the healthcare device or a terminal connected to the healthcare device can record user's biometric information and may further provide additional health information. Particularly, healthcare appcessories capable of providing a user with special experiences and services by being connected to applications of a terminal are leading the recent appcessory craze.

However, usability of the healthcare device is enhanced so far, whereas utilization or accessibility of the healthcare device is increasingly enhanced. For instance, it is still inconvenient for a user of the healthcare device to use the healthcare device in a manner of standing in position determined by the healthcare device or working on a determined posture. If the user fails to use the healthcare device in the determined position or the determined posture, it may cause a problem that biometric information cannot be measured.

Moreover, as the healthcare device tends to be equipped with a physical key for the design matter or the simple configuration, when a user uses the healthcare device, it is inconvenient for the user to use a separate connected terminal or other manipulating means in order to manipulate the healthcare device.

SUMMARY OF THE INVENTION

Accordingly, embodiments of the present invention are directed to an electronic device and controlling method thereof that substantially obviate one or more problems due to limitations and disadvantages of the related art.

One object of the present invention is to provide an electronic device and controlling method thereof, by which user's various biometric informations and be measured and outputted.

Another object of the present invention is to provide an electronic device and controlling method thereof, by which user's use directivity is not required for measuring biometric information.

Further object of the present invention is to provide an electronic device and controlling method thereof, by which a user is facilitated to check a measured biometric information in a manner of displaying the measured biometric information in a direction for facilitating the measured biometric information to be checked by the user.

Another further object of the present invention is to provide an electronic device and controlling method thereof, by which various functions can be performed in response to user's weight center shift for the electronic device without an input key or device so as to provide the user with an intuitive input means.

Technical tasks obtainable from the present invention are non-limited by the above-mentioned technical tasks. And, other unmentioned technical tasks can be clearly understood from the following description by those having ordinary skill in the technical field to which the present invention pertains.

Additional advantages, objects, and features of the invention will be set forth in the disclosure herein as well as the accompanying drawings. Such aspects may also be appreciated by those skilled in the art based on the disclosure herein.

To achieve these objects and other advantages and in accordance with the purpose of the invention, as embodied and broadly described herein, an electronic device according to one embodiment of the present invention may include a display, a sensor module configured to measure a load corresponding to a user, an electrode module configured to be contacted with a body of the user to enable a current to flow, and a controller configured to recognize an electrode initially contacted with the user's body among a plurality of electrodes included in the electrode module as a first pair, recognize the rest of the electrodes contacted with the user's body as a second pair, measure a current flowing between the recognized first and second pairs, determine a biometric information of the user based on the measured current and load, and output the determined biometric information to the display.

In another aspect of the present invention, as embodied and broadly described herein, a method of operating an electronic device according to one embodiment of the present invention may include recognizing an electrode initially contacted with the user's body among a plurality of electrodes as a first pair, recognizing the rest of the electrodes contacted with the user's body as a second pair, measuring a current flowing between the recognized first and second pairs, determining a biometric information of the user based on the measured current and load, and outputting the determined biometric information.

It is to be understood that both the foregoing general description and the following detailed description are exemplary and explanatory and are intended to provide further explanation of the invention as claimed.

Accordingly, embodiments of the present invention provide various effects and/or features.

First of all, an electronic device according to an embodiment of the present invention can measure user's various biometric informations and the output the measured biometric informations.

Secondly, the present invention can provide an electronic device without user's use directivity for biometric information, thereby enhancing user's use convenience.

Thirdly, the present invention can display measured biometric information in a direction for facilitating the measured biometric information to be checked by the user, thereby enabling the user to check the measured biometric information easily and conveniently.

Finally, the present invention can recognize user's weight center shift and then perform a function according to the recognized weight center shift, thereby providing the user with an intuitive input means. Thus, the present invention can provide the electronic device that can be conveniently used by a user with a simple design.

Additional scope of applicability of the present invention will become clear from the detailed description of the invention in the following. Yet, since it will be apparent to those skilled in the art that various modifications and variations can be made therein without departing from the spirit and scope of the invention, it is to be understood that the following detailed description of the present invention and a specific embodiment such as a preferred embodiment of the present invention are exemplary and explanatory.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. The above and other aspects, features, and advantages of the present invention will become more apparent upon consideration of the following description of preferred embodiments, taken in conjunction with the accompanying drawing figures.

In the drawings:

FIGS. 5 to 8 are diagrams for examples of pair recognition according to various embodiments of the present invention;

FIG. 11 is a diagram for an example of coordinates of a weight center according to various embodiments of the present invention;

FIG. 14 and FIG. 15 are diagrams for examples of a biometric information output in response to a weight center shift according to various embodiments of the present invention;

FIG. 16 and FIG. 17 are diagrams for examples of a confirm or cancel input in response to a weight center shift according to various embodiments of the present invention;

FIGS. 18 to 20 are diagrams for examples of a biometric information display corresponding to a weight center shift according to various embodiments of the present invention;

DETAILED DESCRIPTION OF THE INVENTION

Figure 1:
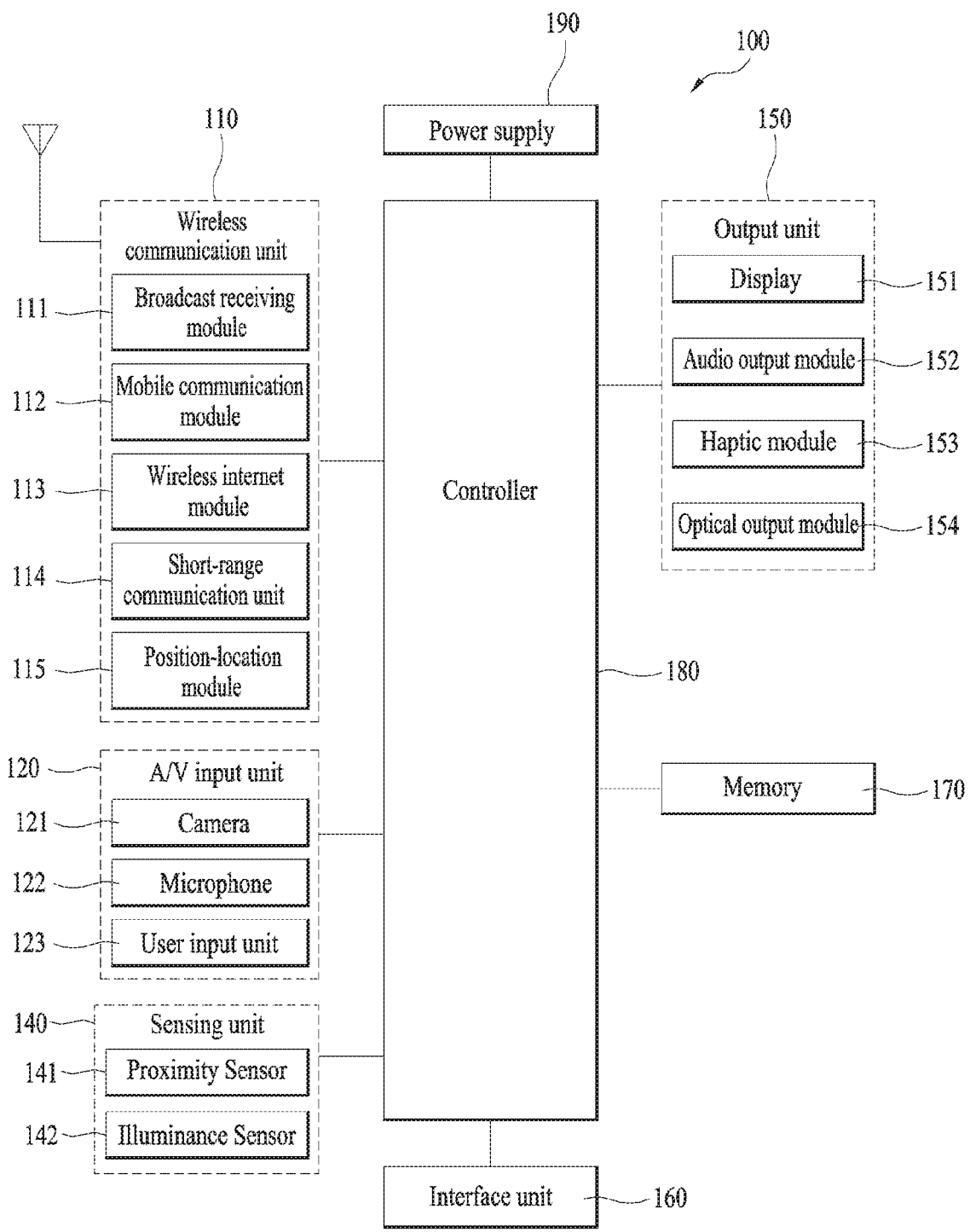
FIG. 1 is a block diagram to describe an electronic device in association with the present invention.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

An electronic device disclosed in the present specification may include a terminal such as a mobile phone, a smartphone, a laptop computer, a digital broadcast terminal, a PDA (personal digital assistants), PMP (portable multimedia player), a navigation, a slate PC, a tablet PC, a ultrabook, a wearable device (e.g., a smartwatch, a smart glass, a head mounted display) (HMD), etc.).

Moreover, a healthcare device may be included in an electronic device described in the present specification. The healthcare device may include a biometric information measuring device configured to measure user's biometric information. For instance, the biometric information measuring device may measure various kinds of biometric informations such as weight, blood pressure, body fat, muscle mass, fat mass, body fluid, bone mass, BMI (body mass index), metabolic age, body balance, basal metabolic rate, and the like. The healthcare device may have a general holder type or a wearable device type wearable on user's body. The healthcare device may include a smart healthcare device capable of communicating with other device or an IoT combined device.

And, it is apparent to those skilled in the art that configuration according to an embodiment disclosed in the present specification may be applicable to a fixed electronic device such as a digital TV, a desktop computer, a digital signage or the like except a case applicable to an electronic device only.

FIG. 1 is a block diagram to describe an electronic device in association with the present invention.

An electronic device 100 may include a wireless communication unit 110, an input unit 120, a sensing unit 140, an output unit 150, an interface unit 160, a memory 170, a controller 180, a power supply unit 190 and the like. As the components shown in FIG. 1 are not mandatory for implementation of the electronic device, the electronic device mentioned in the present specification may have components more or less than the above-listed components.

Particularly, the wireless communication unit 100 among the components may include at least one module capable of enabling a wireless communication between the electronic device 100 and a wireless communication system, between the electronic device 100 and another electronic device, or between the electronic device 100 and an external server. And, the wireless communication unit 110 may include at least one module configured to connect the electronic device 100 to at least one network.

The wireless communication unit 110 may include at least one of a broadcast receiving module 111, a mobile communication module 112, a wireless internet module 113, a short range communication module 114, a location information module 115 and the like.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the electronic device, the surrounding environment of the electronic device, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The electronic device 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the electronic device 100 and a user, as well as function as the user input unit 123 which provides an input interface between the electronic device 100 and the user.

The interface unit 160 serves as an interface with various types of external devices that can be coupled to the electronic device 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the electronic device 100 may perform assorted control functions associated with a connected external device, in response to the external device being connected to the interface unit 160.

The memory 170 is typically implemented to store data to support various functions or features of the electronic device 100. For instance, the memory 170 may be configured to store application programs executed in the electronic device 100, data or instructions for operations of the electronic device 100, and the like. Some of these application programs may be downloaded from an external server via wireless communication. Other application programs may be installed within the electronic device 100 at time of manufacturing or shipping, which is typically the case for basic functions of the electronic device 100 (for example, receiving a call, placing a call, receiving a message, sending a message, and the like). It is common for application programs to be stored in the memory 170, installed in the electronic device 100, and executed by the controller 180 to perform an operation (or function) for the electronic device 100.

The controller 180 typically functions to control overall operation of the electronic device 100, in addition to the operations associated with the application programs. The controller 180 may provide or process information or functions appropriate for a user by processing signals, data, information and the like, which are input or output by the various components depicted in FIG. 1, or activating application programs stored in the memory 170. As one example, the controller 180 controls some or all of the components illustrated in FIG. 1 according to the execution of an application program that have been stored in the memory 170.

The power supply unit 190 can be configured to receive external power or provide internal power in order to supply appropriate power required for operating elements and components included in the electronic device 100. The power supply unit 190 may include a battery, and the battery may be configured to be embedded in the terminal body, or configured to be detachable from the terminal body.

At least one portion of the above-mentioned components can cooperatively operate to implement operations, controls or controlling methods of the electronic device according to various embodiments mentioned in the following description. And, the operations, controls or controlling methods of the electronic device can be implemented on the mobile terminal by running at least one or more application programs saved in the memory 170.

Referring still to FIG. 1, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

A system which generates and transmits a broadcast signal and/or broadcast associated information, or a server which receives a pre-generated broadcast signal and/or broadcast associated information, and sends such items to the electronic device. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this case, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external electronic device, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the electronic device 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the electronic device 100 and a wireless communication system, communications between the electronic device 100 and another electronic device 100, or communications between the electronic device and a network where another electronic device 100 (or an external server) is located, via wireless area networks. One example of the wireless area networks is a wireless personal area networks.

In some embodiments, another electronic device (which may be configured similarly to electronic device 100) may be a wearable device, for example, a smart watch, a smart glass or a head mounted display (HMD), which is able to exchange data with the electronic device 100 (or otherwise cooperate with the electronic device 100). The short-range communication module 114 may sense or recognize the wearable device, and permit communication between the wearable device and the electronic device 100. In addition, when the sensed wearable device is a device which is authenticated to communicate with the electronic device 100, the controller 180, for example, may cause transmission of data processed in the electronic device 100 to the wearable device via the short-range communication module 114. Hence, a user of the wearable device may use the data processed in the electronic device 100 on the wearable device. For example, when a call is received in the electronic device 100, the user may answer the call using the wearable device. Also, when a message is received in the electronic device 100, the user can check the received message using the wearable device.

The location information module 115 is generally configured to detect, calculate, derive or otherwise identify a position of the electronic device. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the electronic device.

As one example, when the electronic device uses a GPS module, a position of the electronic device may be acquired using a signal sent from a GPS satellite. As another example, when the electronic device uses the Wi-Fi module, a position of the electronic device can be acquired based on information related to a wireless access point (AP) which transmits or receives a wireless signal to or from the Wi-Fi module.

The input unit 120 may be configured to permit various types of input to the electronic device 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the electronic device 100. As another example, the cameras 121 may be located in a stereoscopic arrangement to acquire left and right images for implementing a stereoscopic image.

The microphone 122 is generally implemented to permit audio input to the electronic device 100. The audio input can be processed in various manners according to a function being executed in the electronic device 100. If desired, the microphone 122 may include assorted noise removing algorithms to remove unwanted noise generated in the course of receiving the external audio.

The user input unit 123 is a component that permits input by a user. Such user input may enable the controller 180 to control operation of the electronic device 100. The user input unit 123 may include one or more of a mechanical input element (for example, a key, a button located on a front and/or rear surface or a side surface of the electronic device 100, a dome switch, a jog wheel, a jog switch, and the like), or a touch-input, among others. As one example, the touch-sensitive input may be a virtual key or a soft key, which is displayed on a touch screen through software processing, or a touch key which is located on the electronic device at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the electronic device, surrounding environment information of the electronic device, user information, or the like. The controller 180 generally cooperates with the sending unit 140 to control operation of the electronic device 100 or execute data processing, a function or an operation associated with an application program installed in the electronic device based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact.

The proximity sensor 141 may be arranged at an inner region of the electronic device covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the electronic device 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the electronic device 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the electronic device 100. For example, the display unit 151 may display execution screen information of an application program executing at the electronic device 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term " thumbnail " may be used to refer to a reduced image or a reduced still image. A generated left image thumbnail and right image thumbnail may be displayed with a horizontal distance difference therebetween by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the electronic device 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the electronic device 100.

An optical output module 154 can output a signal for indicating an event generation using light of a light source. Examples of events generated in the electronic device 100 may include message reception, call signal reception, a missed call, an alarm, a schedule notice, an email reception, information reception through an application, and the like.

A signal output by the optical output module 154 may be implemented in such a manner that the electronic device emits monochromatic light or light with a plurality of colors. The signal output may be terminated as the electronic device senses that a user has checked the generated event, for example.

The interface unit 160 serves as an interface for external devices to be connected with the electronic device 100. For example, the interface unit 160 can receive data transmitted from an external device, receive power to transfer to elements and components within the electronic device 100, or transmit internal data of the electronic device 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the electronic device 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the electronic device 100 is connected with an external cradle, the interface unit 160 can serve as a passage to allow power from the cradle to be supplied to the electronic device 100 or may serve as a passage to allow various command signals input by the user from the cradle to be transferred to the electronic device there through. Various command signals or power input from the cradle may operate as signals for recognizing that the electronic device is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The electronic device 100 may also be operated in relation to a network storage device that performs the storage function of the memory 170 over a network, such as the Internet.

The controller 180 may typically control the general operations of the electronic device 100. For example, the controller 180 may set or release a lock state for restricting a user from inputting a control command with respect to applications when a status of the electronic device meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the electronic device 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

An electronic device according to various embodiments of the present invention may include a healthcare device capable of measuring user's biometric information. Such an electronic device may include the aforementioned electronic device 100 or some components thereof only. A configuration of an electronic device is described with reference to FIG. 2 as follows.

Figure 2:
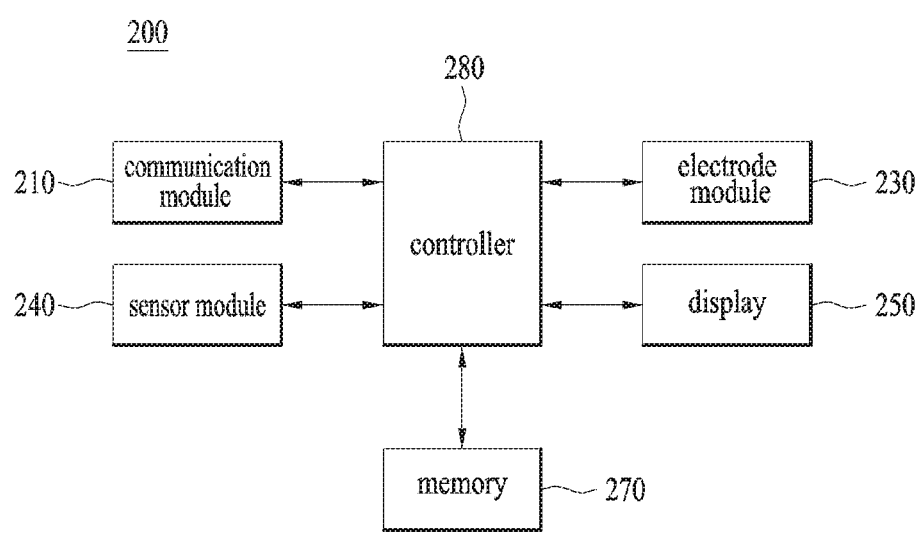
FIG. 2 is a block diagram for the configuration of an electronic device according to one embodiment of the present invention.

FIG. 2 is a block diagram to illustrate a configuration of an electronic device according to various embodiments of the present invention.

Referring to FIG. 2, an electronic device 200 may include a communication module 210, an electrode module 230, a sensor module 240, a display 250, a memory 270 and a controller 280. And, the electronic device 200 may have components more or less than the above-listed components.

The communication module 210 may include at least one module capable of enabling a wireless communication between the electronic device 200 and a wireless communication system, between the electronic device 200 and another electronic device 100/200, or between the electronic device 200 and an external server. And, the communication module 210 may include at least one module configured to connect the electronic device 200 to at least one network. And, the communication module 210 may correspond to the aforementioned wireless communication unit 110.

The electrode module 230 may enable a current to flow through a body of a contacted user and measure the flowing current. For instance, the electrode module 230 may enable a micro current to flow from one of a plurality of electrodes to another electrode or from one electrode pair to another electrode pair through the user's body. And, the electrode module 230 may measure the micro current flowing through the user's body.

The sensor module 240 may sense various informations related to a user's body. For instance, the sensor module 240 may include at least one load cell and then measure user's weight.

The sensor module 240 may include at least one sensor configured to sense at least one of internal information of the electronic device 200, ambient environment information surrounding the electronic device 200, and user information. For example, the sensor module 240 may include at least one of a proximity sensor, an illumination sensor 142, a touch sensor, an acceleration sensor, a magnetic sensor, a G-sensor, a gyroscope sensor, a motion sensor, an RGB sensor, an infrared (IR) sensor, a finger scan sensor, an ultrasonic sensor, an optical sensor (e.g., a camera), a microphone, a battery gauge, an environment sensor (e.g., a barometer, a hygrometer, a thermometer, a radiation detection sensor, a thermal sensor, and a gas sensor, etc.), and a chemical sensor (e.g., an electronic nose, a healthcare sensor, a biometric sensor, etc.). The electronic device disclosed in the present specification may be configured to combine to utilize informations sensed by at least two of the above sensors. And, the electrode module 230 and the sensor module 240 may correspond to the aforementioned sensing unit 140.

The display 250 is typically configured to display (output) information processed by the electronic device 200. For example, the display 250 may display the measured biometric information. And, the display unit 250 may display a running screen information of an application program running on the electronic device 200 or a user interface/graphic user interface (UI/GUI) information according to the running screen information.

Since the display 200 may include a plurality of displays, a plurality of the displays may be provided to the electronic device 200. For instance, a plurality of the displays 250 may be disposed in a plurality of directions of the electronic device 200, respectively. As at least one of a plurality of the devices respectively disposed in a plurality of the directions is turned, information may be displayed on the turned-on at least one display. If the display 250 is turned off, it may look identical to a case of the electronic device 200. Hence, the electronic device 200 may be provided with the display 250 of a type difficult to be recognized by a user if the display unit 250 is turned off. Hence, in case that a plurality of the displays 250 are provided, a user may have difficult in recognizing the rest of the displays other than the turned-on display.

The memory 170 is typically implemented to store data to support various functions or features of the electronic device 200. For instance, the memory 270 may be configured to store a multitude of application programs runnable in the electronic device 200, data or instructions for operations of the electronic device 100, and the like. Some of these application programs may be downloaded from an external server by wireless communication. At least one portion of the application programs for basic functions (e.g., biometric information measurement function, weight center measurement function, information display function, etc.) may be already installed on the electronic device 200 at time of manufacturing or shipping. It is common for application programs to be stored in the memory 170, installed on the electronic device 200, and launched by the controller 180 to perform an operation (or function) for the electronic device 200. And, the memory 270 may correspond to the aforementioned memory 170.

The controller 180 typically functions to control overall operation of the electronic device 200, in addition to the operations associated with the application programs. The controller 180 may provide or process information or functions appropriate for a user by processing signals, data, information and the like, which are inputted or outputted by the various components mentioned in the foregoing description, or activating application programs stored in the memory 170. Detailed operations of the controller 280 shall be described later.

Figure 3:
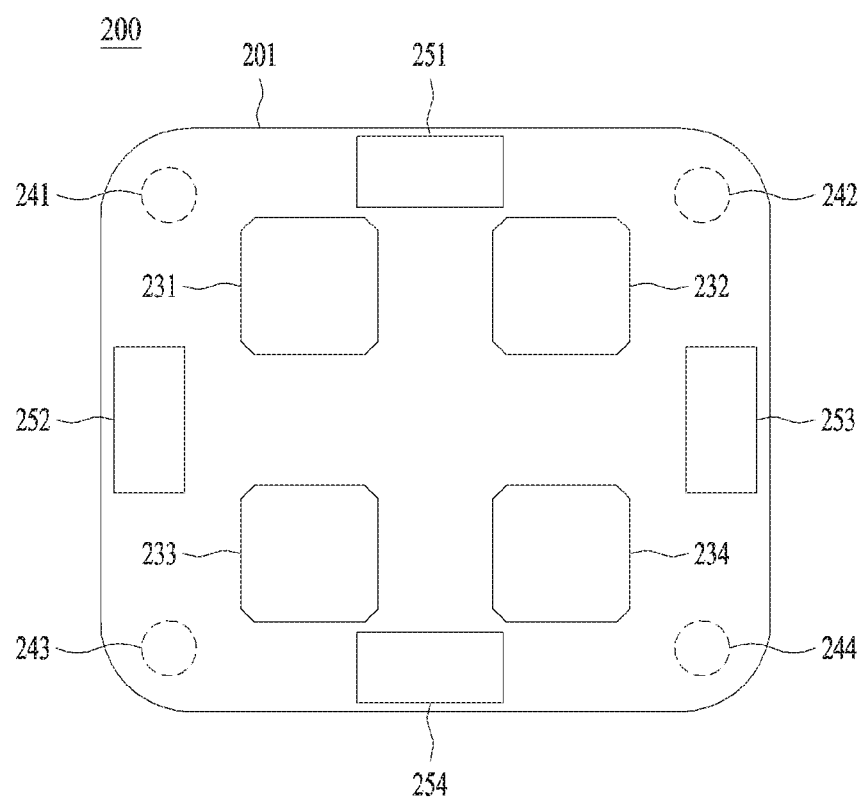
FIG. 3 is a diagram for an example of a configuration of an electronic device according to various embodiments of the present invention.

FIG. 3 is a diagram for an example of a configuration of an electronic device according to various embodiments of the present invention.

Referring to FIG. 3, an electronic device 200 may include a case 201 configuring an exterior thereof. The case 201 may include a plurality of cases and may further include a configuration for the assembly of a plurality of the cases. A configuration for supporting a user may be further included in the case 201 of the electronic device 200. Hence, a user can step on the case 201 of the electronic device 200 in one direction, and the electronic device 200 can measure user's various biometric informations of the stepping-on user.

The electronic device 200 may include a plurality of electrodes 231 to 234, each of which coming into contact with a user's body enables a current to flow therein. Two of a plurality of the electrodes 231 to 234 and the rest of the electrodes are divided into different pairs, respectively. An, a micro current may flow from one pair to the other. And, a plurality of the electrodes 231 to 234 may be included in the aforementioned electrode module 230.

The electronic device 200 may include a plurality of load cells 241 to 244, and each of a plurality of the load cells 241 to 244 can measure a load. Each of a plurality of the load cells 241 to 244 can generate an electrical signal corresponding to an external force (e.g., a load). And, a plurality of the load cells 241 to 244 may be included in the aforementioned sensor module 240.

The electronic device 200 may include a plurality of displays 251 to 254. And, a plurality of the displays 251 to 254 may be disposed in four different directions, respectively. Moreover, a plurality of the displays 251 to 254 can output various informations. As at least one of a plurality of the displays 251 to 254 is turned, it may be able to output information. As mentioned in the foregoing description, when a plurality of the displays 251 to 254 are turned off, they can be disposed so as not to be distinguished from the case 201.

Figure 4:
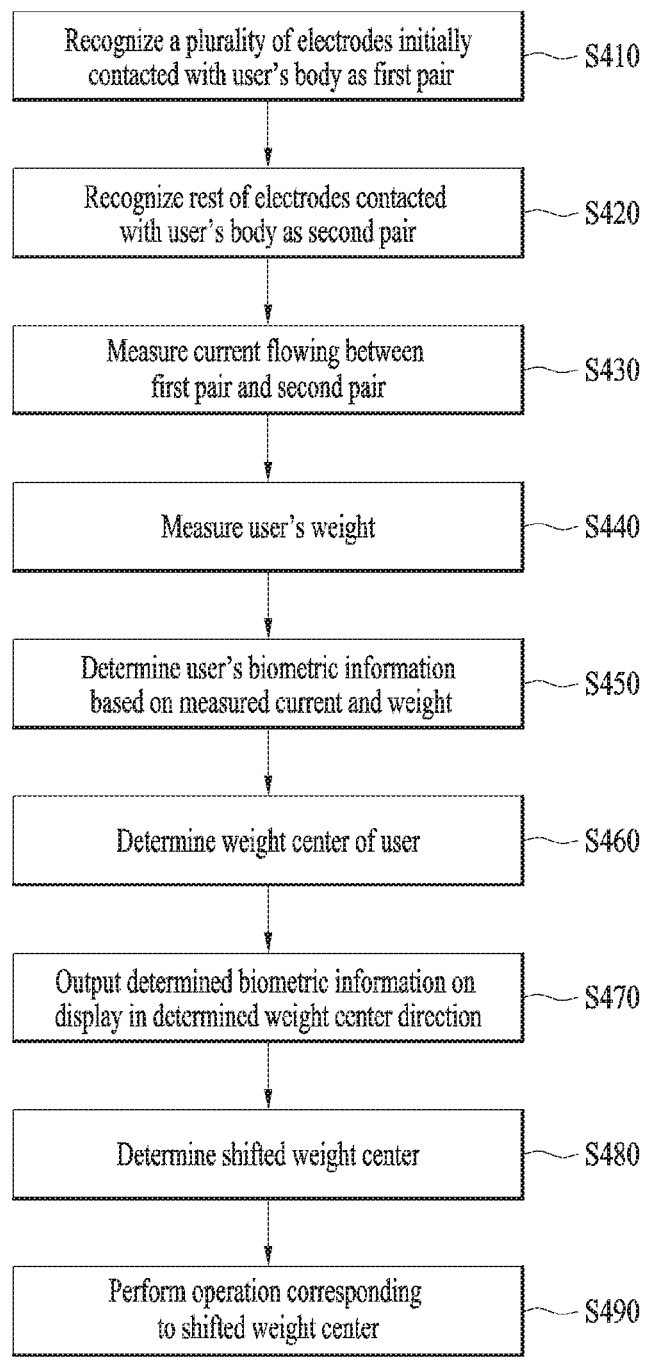
FIG. 4 is a flowchart for a method of operating an electronic device according to various embodiments of the present invention.

FIG. 4 is a flowchart for a method of operating an electronic device according to various embodiments of the present invention.

Referring to FIG. 4, the electronic device 200 may recognize a plurality of electrodes initially contacted with a user's body as a first pair [S410]. And, the electronic device 200 may recognize the rest of electrodes contacted with the user's body as a second pair [S420].

If the electronic device 200 is configured to enable a user to step thereon, a plurality of the electrodes 231 to 234 can be provided to a plane on which the user steps. The controller 280 of the display device 200 may recognize a plurality of the electrodes initially contacted with the user's body among a plurality of the electrodes 231 to 234 as the first pair and also recognize a plurality of the electrodes subsequently contacted with the user's body as the second pair. For instance, when both foots of the user are contacted with a plurality of the electrodes 231 to 234 of the electronic device 200, a plurality of the electrodes initially contacted with the foot first stepping on the electronic device 200 may be recognized as the first pair and a plurality of the electrodes contacted with the other foot stepping on the electric device 200 later may be recognized as the second pair. This is described in detail with reference to FIGS. 5 to 8.

FIGS. 5 to 8 are diagrams for examples of pair recognition according to various embodiments of the present invention.

Referring to FIG. 5, the electronic device 200 may include a plurality of the electrodes 231 to 234, and a plurality of the electrodes 231 to 234 may correspond to a plane on which a user steps. When a user steps on the electronic device 200 for biometric information measurement, if a user's left foot steps on the electronic device 200 first, the first and third electrodes 231 and 233 corresponding to the user's left foot among a plurality of the electrodes 231 to 234 can be contacted with the left foot. As the first and third electrodes 231 and 233 are contacted with the left foot, the controller 280 may recognize the first and third electrodes 231 and 233 as one pair, e.g., a first pair 51. Subsequently, if the other foot of the user, i.e., the right foot steps on the electronic device 200, the second and fourth electrodes 232 and 234 corresponding to the user's right foot among a plurality of the electrodes can be contacted with the right foot. As the second and fourth electrodes 232 and 234 are contacted with the right foot, the controller 280 may recognize the second and fourth electrodes 232 and 234 as another pair, e.g., a second pair 52. Hence, a current can flow between the first pair 51 and the second pair 52. And, each of a plurality of the load cells 241 to 244 can measure a weight of the user stepping on the electronic device 200.

Referring to FIG. 6, the electronic device 200 may include a plurality of the electrodes 231 to 234, and a plurality of the electrodes 231 to 234 may correspond to a plane on which a user steps. When a user steps on the electronic device 200 for biometric information measurement, if a user's left foot steps on the electronic device 200 first, the first and second electrodes 231 and 232 corresponding to the user's left foot among a plurality of the electrodes 231 to 234 can be contacted with the left foot. As the first and second electrodes 231 and 232 are contacted with the left foot, the controller 280 may recognize the first and second electrodes 231 and 232 as one pair, e.g., a first pair 61. Subsequently, if the other foot of the user, i.e., the right foot steps on the electronic device 200, the third and fourth electrodes 233 and 234 corresponding to the user's right foot among a plurality of the electrodes can be contacted with the right foot. As the third and fourth electrodes 233 and 234 are contacted with the right foot, the controller 280 may recognize the third and fourth electrodes 233 and 234 as another pair, e.g., a second pair 62. Hence, a current can flow between the first pair 61 and the second pair 62. And, each of a plurality of the load cells 241 to 244 can measure a weight of the user stepping on the electronic device 200.

Referring to FIG. 7, the electronic device 200 may include a plurality of the electrodes 231 to 234, and a plurality of the electrodes 231 to 234 may correspond to a plane on which a user steps. When a user steps on the electronic device 200 for biometric information measurement, if a user's left foot steps on the electronic device 200 first, the third and fourth electrodes 233 and 234 corresponding to the user's left foot among a plurality of the electrodes 231 to 234 can be contacted with the left foot. As the third and fourth electrodes 233 and 234 are contacted with the left foot, the controller 280 may recognize the third and fourth electrodes 233 and 234 as one pair, e.g., a first pair 71. Subsequently, if the other foot of the user, i.e., the right foot steps on the electronic device 200, the first and second electrodes 231 and 232 corresponding to the user's right foot among a plurality of the electrodes can be contacted with the right foot. As the first and second electrodes 231 and 232 are contacted with the right foot, the controller 280 may recognize the first and second electrodes 231 and 232 as another pair, e.g., a second pair 72. Hence, a current can flow between the first pair 71 and the second pair 72. And, each of a plurality of the load cells 241 to 244 can measure a weight of the user stepping on the electronic device 200.

Referring to FIG. 8, the electronic device 200 may include a plurality of the electrodes 231 to 234, and a plurality of the electrodes 231 to 234 may correspond to a plane on which a user steps. When a user steps on the electronic device 200 for biometric information measurement, if a user's left foot steps on the electronic device 200 first, the second and fourth electrodes 232 and 234 corresponding to the user's left foot among a plurality of the electrodes 231 to 234 can be contacted with the left foot. As the second and fourth electrodes 232 and 234 are contacted with the left foot, the controller 280 may recognize the second and fourth electrodes 232 and 234 as one pair, e.g., a first pair 81. Subsequently, if the other foot of the user, i.e., the right foot steps on the electronic device 200, the first and third electrodes 231 and 233 corresponding to the user's right foot among a plurality of the electrodes can be contacted with the right foot. As the first and third electrodes 231 and 233 are contacted with the right foot, the controller 280 may recognize the first and third electrodes 231 and 233 as another pair, e.g., a second pair 82. Hence, a current can flow between the first pair 51 and the second pair 52. And, each of a plurality of the load cells 241 to 244 can measure a weight of the user stepping on the electronic device 200.

Meanwhile, the above description of the pair recognition is exemplary, by which the present invention is non-limited. According to the above description, the user's left foot steps on the electronic device 200 first. Yet, the user's right foot may step on the electronic device 200 first. If the right foot steps on the electronic device 200 first, the electrodes contacted with the right foot may become a first pair and other electrodes contacted with the left foot may become a second pair. In configuring a plurality of pairs to enable a current to flow therebetween, apparently, there is no difference no matter when a user's right or left foot steps on the electronic device 200 first.

As mentioned in the foregoing description, depending on being contacted with a user's body stepping on the electronic device 200, the electronic device 200 may recognize a plurality of the electrodes 231 to 234 as a first pair and a second pair and enable a micro current to flow between the recognized first and second pairs. According to a related art healthcare device having electrodes, a user should step in a determined direction or on a determined electrode. Yet, the electronic device 200 according to the present invention is non-directional, i.e., a direction in which a user should step or an electrode on which a user should step is not determined. Hence, when a user steps on the electronic device 200 in any direction, the electronic device 200 can measure biometric information.

FIG. 4 is referred to again.

The electronic device 200 may measure the current flowing between the recognized first and second pairs [S430].

The controller 280 of the electronic device 200 may control a micro current to flow between the electrode of the recognized first pair and the electrode of the recognized second pair and then measure the flowing current. Hence, the micro current can flow from the electrode of the first pair to the electrode of the second pair or from the electrode of the second pair to the electrode of the first pair, via the user body. Based on the measured micro current, the controller 280 may measure resistance of the user body, e.g., bioelectrical impedance. This is described in detail with reference to FIG. 9.

Figure 9:
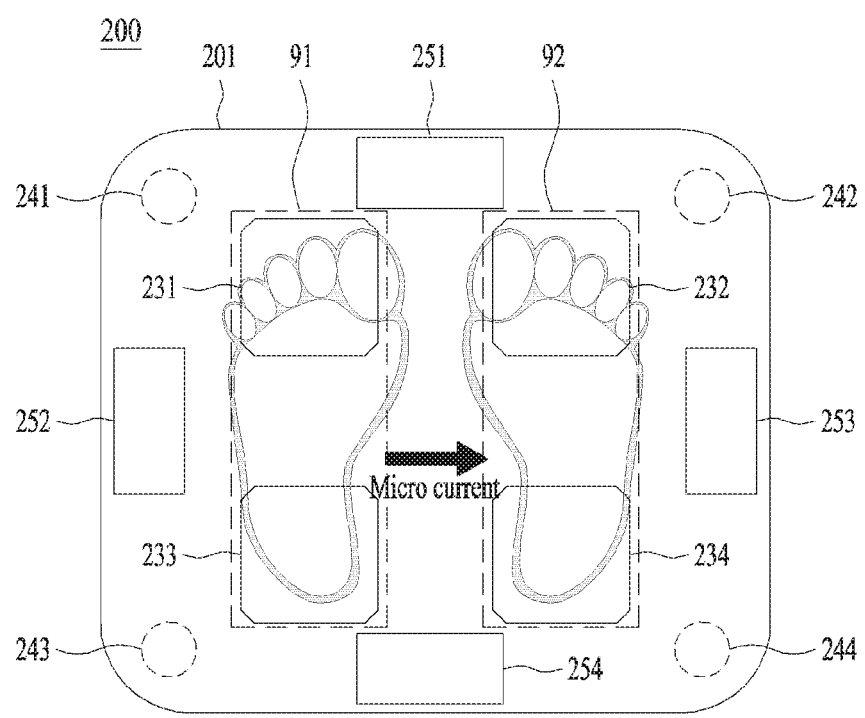
FIG. 9 is a diagram for an example of current flowing between the recognized pairs according to various embodiments of the present invention.

FIG. 9 is a diagram for an example of current flowing between the recognized pairs according to various embodiments of the present invention.

Referring to FIG. 9, in response to contact with a user body, e.g., a contact with foots, the controller 280 of the electronic device 200 may recognize the first and third electrodes 231 and 233 and the second and fourth electrodes 232 and 234 among a plurality of the electrodes 231 to 234 as a first pair 91 and a second pair 92, respectively. A micro current may flow in a direction from the first and third electrodes 231 and 233 of the first pair 91 to the second and fourth electrodes 232 and 234 of the second pair 92. In doing so, the flowing micro current may flow via a user body. Herein, the micro current may include a current on a level unharmful to a user's body. The electronic device 200 may enable the micro current to flow in a direction from the first and third electrodes 231 and 233 of the first pair 91 to the second and fourth electrodes 232 and 234 of the second pair 92. Alternatively, the electronic device 200 may enable the micro current to flow in a direction from the second and fourth electrodes 232 and 234 of the second pair 92 to the first and third electrodes 231 and 233 of the first pair 91. And, the electronic device 200 (e.g., controller 280, electrode module 230) may measure the flowing micro current. Based on the measured micro current, the controller 280 may measure resistance of the user body, e.g., bioelectrical impedance.

FIG. 4 is referred to again.

The electronic device 200 may measure a user's weight [S440].

Based on the load measured through each of a plurality of the load cells 241 to 244, the electronic device 200 may measure the user's weight.

Based on the measured current and weight, the electronic device 200 may determine user's biometric information.

For instance, based on the measured micro current and weight, the electronic device 200 can determine user's various biometric informations. For one example, based on the measured micro current, the electronic device 200 may measure bioelectrical impedance and is then able to determine user's biometric information based on the measured bioelectrical impedance and weight. And, the electronic device 200 may determine user's biometric information by further considering previously inputted user information such as age, sex, height, caloric intake, food intake menu, etc. Hence, based on the previously inputted user information, the measured micro current, the measured bioelectrical impedance and the measured weight, the controller 280 of the electronic device 200 may determine user's biometric information. Herein, the user's biometric information may include at least one of weight, blood pressure, body fat, muscle mass, fat mass, body fluid, bone mass, BMI (body mass index), body balance, basal metabolic rate and metabolic age of the user.

In order to determine the user's biometric information, the controller 280 may use a database stored in the memory 270 or various saved formulas.

The electronic device 200 may determine user's weight center [S460].

The controller 280 of the electronic device 200 may determine a weight center of a user stepping on the electronic device 200. For instance, the controller 280 may determine the user's weight center based on the loads respectively measured by a plurality of the load cells 241 to 244. For one example, based on a relative size of the load measured by each of a plurality of the load cells 241 to 244, the controller 280 can determine the user's weight center. Herein, the relative size of the load measured by the load cell may include a relative size of an electrical signal, a voltage or a resistance at each load cell.

This is described in detail with reference to FIG. 10 and FIG. 11.

Figure 10:
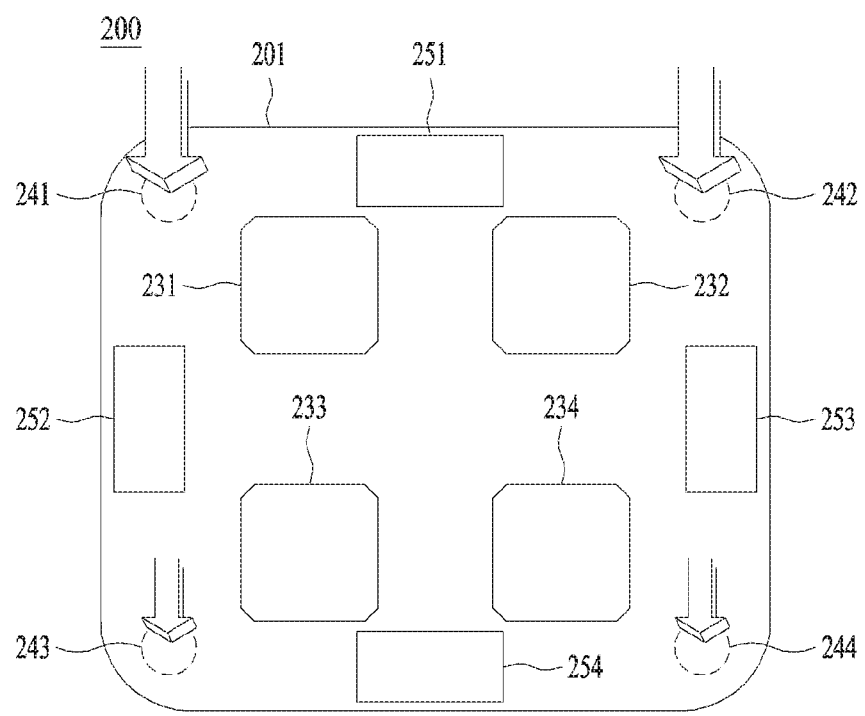
FIG. 10 is a diagram for an example of a load for each of a plurality of load cells according to various embodiments of the present invention.

FIG. 10 is a diagram for an example of a load for each of a plurality of load cells according to various embodiments of the present invention.

FIG. 11 is a diagram for an example of coordinates of a weight center according to various embodiments of the present invention.

Referring to FIG. 10, each of a plurality of the load cells 241 to 244 included in the electronic device 200 may sense a load in response to an occurrence that a user body steps on the electronic device 200. When a user inclines a user's head in a direction of a first display 251 of the electronic device 200, the load sensed by the first and second load cells 241 and 242 may be greater than the load sensed by the third and fourth load cells 243 and 244. Hence, a size of the load sensed by the first and second load cells 241 and 242 may be greater than that of the load sensed by the third and fourth load cells 243 and 244. The controller 180 may display relative sizes of the loads respectively sensed by a plurality of the load cells 241 to 244 in an x-y plane of 2-dimensional coordinate system and then calculate coordinates of a weight center in the x-y plane. Referring to FIG. 11, in the x-y plane corresponding to directions of a plurality of the load cells 241 to 244, the controller 280 may calculate coordinates of a weight center 1110 according to relative sizes of the loads respectively sensed by a plurality of the load cells 241 to 244. Moreover, in order for the coordinates of the weight center 1110 to match the electronic device 200, the controller 280 may rotate the x-y plane or the coordinates of the weight center 1110. Based on the calculated coordinates of the weight center, the controller 280 can determine a user's weight center.

Meanwhile, using a formula, the controller 280 may calculate coordinates of a weight center. Such a formula may include a formula using loads respectively sensed by a plurality of the load cells 241 to 244.

FIG. 4 is referred to again.

The electronic device 200 may output the determined biometric information on a display of the determined weight center direction [S470].

The controller 280 of the electronic device 200 may output the determined biometric information to the display of the determined weight center direction among a plurality of the displays 250. As mentioned in the foregoing description, since a direction of inclining a user's head is a weight center direction, the electronic device 200 may output biometric information on a display of the weight center direction that is a direction in which a user can view the biometric information.

This is described with reference to FIG. 12 and FIG. 13.

Figure 12:
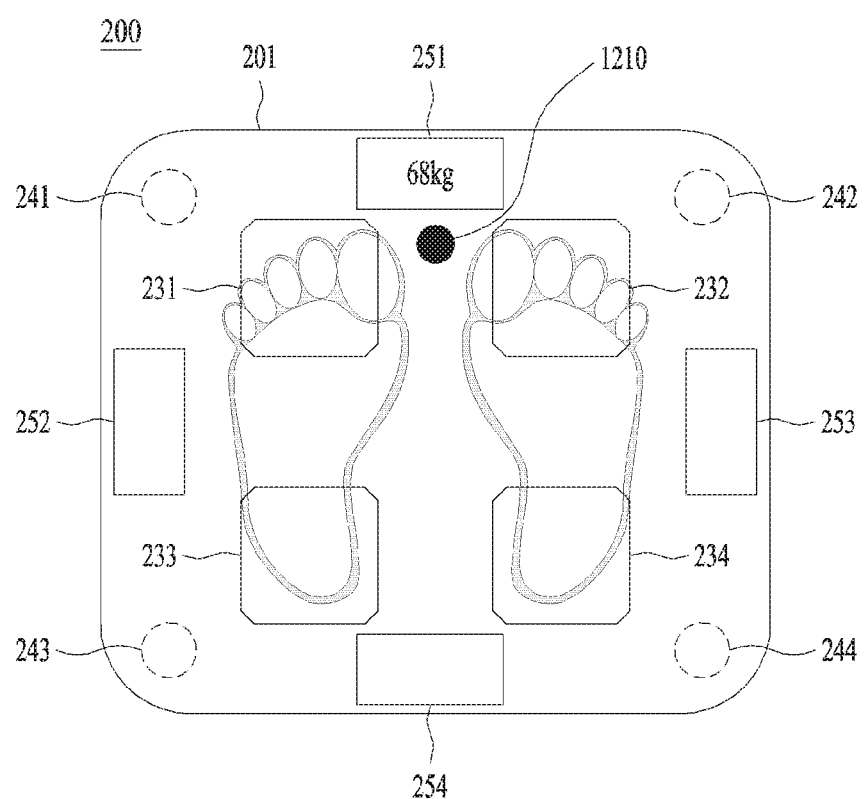
FIG. 12 and FIG. 13 are diagrams for examples of a biometric information output according to various embodiments of the present invention.
Figure 13:
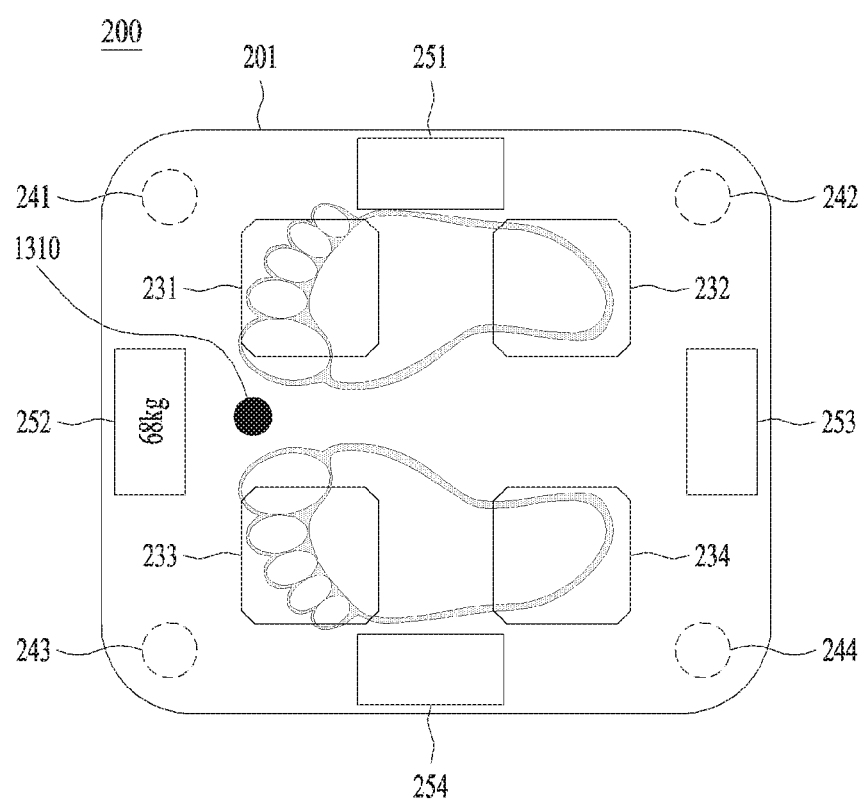

FIG. 12 and FIG. 13 are diagrams for examples of a biometric information output according to various embodiments of the present invention.

Referring to FIG. 12, the electronic device 200 may include a plurality of the displays 251 to 254. And, a plurality of the displays 251 to 254 may be located in different directions, e.g., four directions with reference to a center of the electronic device 200, respectively. Based on the loads respectively sensed by a plurality of the load cells 241 to 244, the electronic device 200 may determine a user's weight center. For instance, as shown in FIG. 12, the controller 280 may determine that the user's weight center 1210 is located in a direction of the first display 251. Hence, the controller 280 may output the user's measured biometric information to the first display 251. For instance, the controller 280 can output the measured weight to the first display 251. In doing so, the electronic device 200 may turn on the first display 251 only but turn off the rest of the displays 252 to 254.

Referring to FIG. 13, the electronic device 200 may include a plurality of the displays 251 to 254. And, a plurality of the displays 251 to 254 may be located in different directions, e.g., four directions with reference to a center of the electronic device 200, respectively. Based on the loads respectively sensed by a plurality of the load cells 241 to 244, the electronic device 200 may determine a user's weight center. For instance, as shown in FIG. 13, the controller 280 may determine that the user's weight center 1210 is located in a direction of the second display 252. Hence, the controller 280 may output the user's measured biometric information to the second display 252. For instance, the controller 280 can output the measured weight to the second display 252. In doing so, the electronic device 200 may turn on the second display 252 only but turn off the rest of the displays 251, 253 and 254.

Thus, the electronic device 200 may output the measured biometric information to the display 250 of the user's weight center direction. Herein, the user's weight center may include a user's weight center initially determined by the electronic device 200 after the user has stepped on the electronic device 200. In the following description, the user's weight center initially determined after the user's stepping-on shall be named an initial weight center.

Meanwhile, the controller 280 may control a plurality of determined biometric informations to be displayed on the display 250 in sequence. For instance, the controller 280 can display a plurality of the determined biometric informations (e.g., weight, BMI, body fat, muscle mass, fat mass, body fluid, bone mass, etc.) on the display 250 of the weight center direction in sequence. Therefore, the electronic device 200 according to various embodiments of the present invention can output various biometric informations through the display 250 even if a screen size of the display 250 is limited.

FIG. 4 is referred to again.

The electronic device 200 may determine a user's shifted weight center [S480] and then perform an operation corresponding to the shifted weight center [S490].

The controller 280 of the electronic device 200 may determine a shifted weight center according to a shift of a user's weight center based on a load sensed by the sensor module 240, e.g., each of a plurality of the load cells 241 to 244. Herein, the weight center shift may mean that an initial weight center is shifted to another weight center. And, the weight center shift may mean that a user applies a force in a specific direction as well as that a user's weight center is shifted.

The controller 280 of the electronic device 200 may perform various operations corresponding to a shifted weight center.

For one example, as an operation corresponding to a shifted weight center, the electronic device 200 may output an information different from a previously displayed information on a display of an initial weight center direction. This is described with reference to FIG. 14 and FIG. 15.

FIG. 14 and FIG. 15 are diagrams for examples of a biometric information output in response to a weight center shift according to various embodiments of the present invention.

Referring to FIG. 14, the electronic device 200 may determine a first weight center 1410 that is an initial weight center, and then output a first biometric information, e.g., a weight, on the first display 251 in a direction of the first weight center 1410. According to a user's weight center shift, the electronic device 200 may determine a second weight center 1411 that is a shifted weight center. As the weight center is shifted from the first weight center 1410 to the second weight center 1411, if the weight center is shifted in a left direction, the controller 280 may display a second biometric information, e.g., BMI on the first display 251. Herein, the second biometric information may include a biometric information having an order previous to that of the first biometric information among a plurality of biometric informations having sequential orders. Thus, in response to a user's weight center shift, the electronic device 200 may change a biometric information outputted to the display 250 into another biometric information and then output the changed biometric information.

Referring to FIG. 15, the electronic device 200 may determine a first weight center 1510 that is an initial weight center, and then output a first biometric information, e.g., a weight, on the first display 251 in a direction of the first weight center 1510. According to a user's weight center shift, the electronic device 200 may determine a third weight center 1512 that is a shifted weight center. As the weight center is shifted from the first weight center 1510 to the third weight center 1512, if the weight center is shifted in a right direction, the controller 280 may display a third biometric information, e.g., body fat on the first display 251. Herein, the third biometric information may include a biometric information having an order next to that of the first biometric information among a plurality of biometric informations having sequential orders. Thus, in response to a user's weight center shift, the electronic device 200 may change a biometric information outputted to the display 250 into another biometric information and then output the changed biometric information.

Meanwhile, in response to an extent of a user's weight center shift, the electronic device 200 may change a displayed biometric information into another biometric information and then output the changed biometric information. For instance, if a weight center shift of a prescribed direction occurs, the electronic device 200 can change a displayed biometric information into another biometric information in response to a shifted distance and then output the changed biometric information. For one example, when a weight center is shifted in a left direction, if the weight center is shifted by a first distance, the electronic device 200 can output a second biometric information. Or, if the weight center is shifted by a second distance, the electronic device 200 can output a fourth biometric information. Herein, the second biometric information and the fourth biometric information may be different from each other.

For another example, as an operation corresponding to a shifted weight center, the electronic device 200 may apply an input such as Confirm or Cancel, Basic Screen Display or Previous Screen Display, or the like. This is described with reference to FIG. 16 and FIG. 17.

FIG. 16 and FIG. 17 are diagrams for examples of a confirm or cancel input in response to a weight center shift according to various embodiments of the present invention.

Referring to FIG. 16, the electronic device 200 may output a message for requesting user's confirmation to the first display 251 in a direction of a first weight center 1610 that is an initial weight center. In response to a shift of a user's weight center, the electronic device 200 may determine a second weight center 1611 that is a shifted weight center. As the weight center is shifted from the first weight center 1610 to the second weight center 1611, if the weight center is shifted in a left direction, the controller 280 may apply a confirmation input (YES). Hence, the confirmation input (YES) for the requested message can be applied to the first display 251.

Referring to FIG. 17, the electronic device 200 may output a message for requesting user's confirmation to the first display 251 in a direction of a first weight center 1710 that is an initial weight center. In response to a shift of a user's weight center, the electronic device 200 may determine a third weight center 1712 that is a shifted weight center. As the weight center is shifted from the first weight center 1710 to the third weight center 1712, if the weight center is shifted in a right direction, the controller 280 may apply a cancellation input (NO). Hence, the cancellation input (NO) for the requested message can be applied to the first display 251.

Thus, although a separate physical key is provided to the electronic device 200 or a different device (e.g., terminal (not shown)) is not connected to the electronic device, the electronic device 200 can recognize a user's weight center shift as one of various inputs such as an input for outputting another biometric information, a confirmation input, a cancellation information and the like. Therefore, the electronic device 200 according to various embodiments of the present invention can perform functions according to user's various manipulations by maintaining a simple design.

In response to a user's weight center shift, the electronic device 200 according to various embodiments of the present invention can output past or expected future information of a biometric information displayed on the display 250.

For instance, if the user's weight center is shifted in a left direction, the electronic device 200 can output a past information of a displayed biometric information in response to a shifted distance. And, if the user's weight center is shifted in a right direction, the electronic device 200 can output an expected future information of the displayed biometric information in response to a shifted distance.

In response to a distance or angle of a shifted weight center, the electronic device 200 may output a past biometric information or an expected future biometric information. For instance, if the distance of the shifted weight center becomes longer, the electronic device 200 may output a biometric information of the older past or a biometric information of a farther future. For example, if a distance of a shifted weight center is a first distance, the electronic device 200 may output a weight of 1 month ago. And, if a distance of a shifted weight center is a third distance, the electronic device 200 may output a weight of 3 months ago. For another example, if a distance of a shifted weight center is a first distance, the electronic device 200 may output a weight of 1 month later. And, if a distance of a shifted weight center is a third distance, the electronic device 200 may output a weight of 3 months later. Herein, the third distance may be greater than the first distance.

This is described with reference to FIGS. 18 to 20.

FIGS. 18 to 20 are diagrams for examples of a biometric information display corresponding to a weight center shift according to various embodiments of the present invention.

Referring to FIG. 18, the electronic device 200 may output a current weight to the first display 251 that is a display in a direction of a first weight center 1810 that is an initial weight center. In response to a user's weight center shift, the electronic device 200 may determine a third weight center 1813 that is a shifted weight center. As the weight center is shifted from the first weight center 1810 to the third weight center 1813, if the weight center is shifted in a left direction, the controller 280 may output a past weight. For instance, based on data stored in the memory 270 or data transmitted from a server (not shown), the controller 280 may output a past weight to the first display 251. In response to a distance or angle of the shifted weight center, the electronic device 200 may output a past biometric information. For instance, if a distance of the shifted weight center gets longer, the electronic device 200 may output a biometric information of an older past. For one example, in response to a distance of the shifted weight center, e.g., a distance between the first weight center 1810 and the third weight center 1813, the electronic device 200 may output a user's weight of 2 weeks ago.

Referring to FIG. 19, the electronic device 200 may output a current weight to the first display 251 that is a display in a direction of a first weight center 1910 that is an initial weight center. In response to a user's weight center shift, the electronic device 200 may determine a fourth weight center 1914 that is a shifted weight center. As the weight center is shifted from the first weight center 1910 to the fourth weight center 1914, if the weight center is shifted in a left direction, the controller 280 may output a past weight. For instance, based on data stored in the memory 270 or data transmitted from a server (not shown), the controller 280 may output a past weight to the first display 251. In response to a distance or angle of the shifted weight center, the electronic device 200 may output a past biometric information. For instance, if a distance of the shifted weight center gets longer, the electronic device 200 may output a biometric information of an older past. For one example, in response to a distance of the shifted weight center, e.g., a distance between the first weight center 1910 and the fourth weight center 1914, the electronic device 200 may output a user's weight of 3 months ago.

Referring to FIG. 20, the electronic device 200 may output a current weight to the first display 251 that is a display in a direction of a first weight center 2010 that is an initial weight center. In response to a user's weight center shift, the electronic device 200 may determine a fifth weight center 2015 that is a shifted weight center. As the weight center is shifted from the first weight center 2010 to the fifth weight center 2015, if the weight center is shifted in a right direction, the controller 280 may output an expected future weight. For instance, based on data stored in the memory 270 or data transmitted from an server (not shown), the controller 280 may calculate an expected future weight using user's past and current weights and then output the expected future weight to the first display 251.

Thus, the electronic device 200 according to various embodiments of the present invention can output past or expected future information of biometric information displayed on the display 250 in response to a user's weight center shift.

Based on a user's weight center shift, the electronic device 200 according to various embodiments of the present invention may measure a user's body balance. This is described with reference to FIG. 21.

Figure 21:
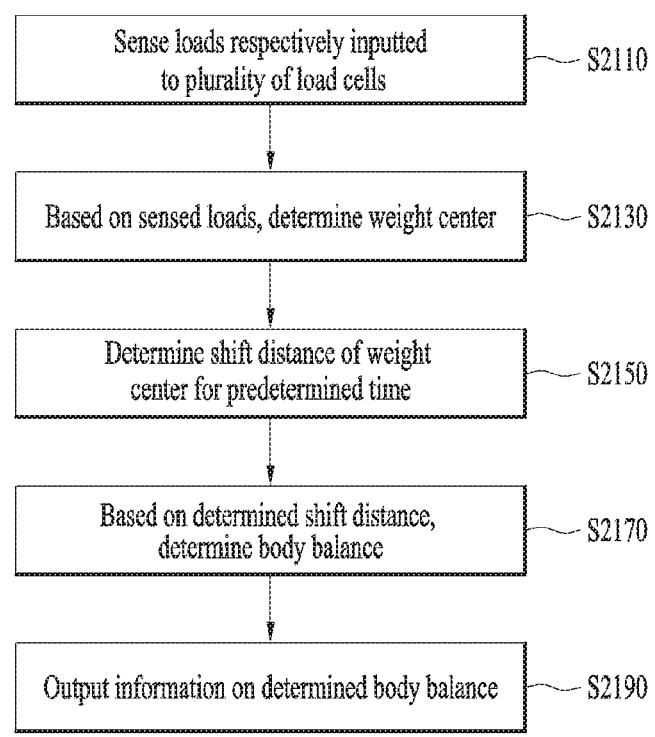
FIG. 21 is a flowchart for a body balance determination operation of an electronic device according to various embodiments of the present invention.

FIG. 21 is a flowchart for a body balance determination operation of an electronic device according to various embodiments of the present invention.

Referring to FIG. 21, according to a user stepping on the electronic device 200, the electronic device 200 may sense loads respectively inputted to a plurality of the load cells 241 to 244 [S2110]. Based on the sensed loads, the electronic device 200 may determine a weight center [S2130] and also determine a shift distance of the weight center shifted for a predetermined time [S2150]. For instance, the electronic device 200 may determine a weight center of the user stepping on the electronic device 200 every 1 second and also determine a total shift distance of the weight center having been shifted for 10 seconds. Based on the determined shift distance, the electronic device 200 may determine a user's body balance [S2170] and then output information on the determined body balance [S2190]. For instance, if the determined shift distance gets longer, the electronic device 200 may determine that the user's body balance becomes poorer. If the determined shift distance gets shorter, the electronic device 200 may determine that the user's body balance becomes better. And, the electronic device 200 may output the determined body balance with various references to numerical values, grades and the like. Moreover, the electronic device 200 may output the user's determined body balance through the display unit 250 and also send it to another device.

The electronic device 200 according to various embodiments of the present invention may be embodied into various shapes. Therefore, like the drawings of the above description, the electronic device 200 may have a rectangular shape or one of other shapes. For instance, the electronic device 200 may have a circular shape.

Figure 22:
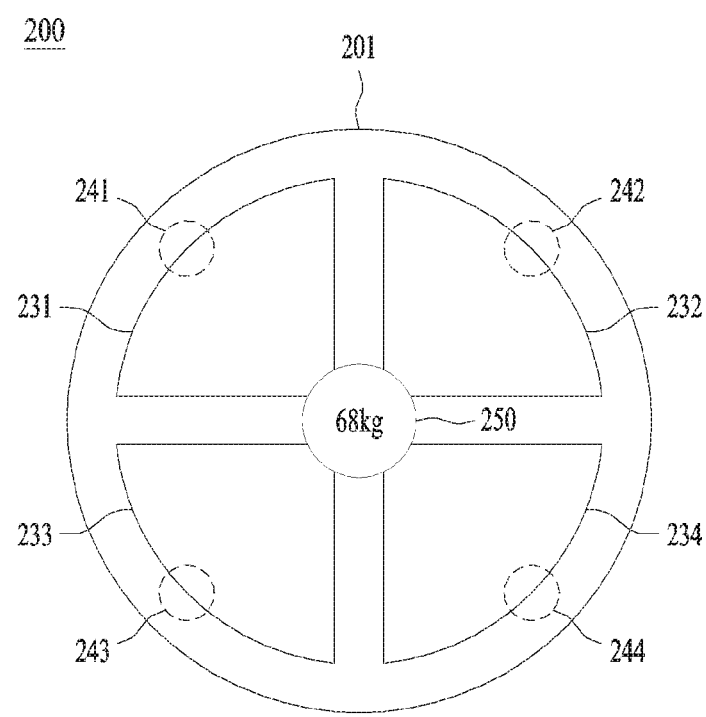
FIG. 22 is a diagram for an example of a circular electronic device according to various embodiments of the present invention.

FIG. 22 is a diagram for an example of a circular electronic device according to various embodiments of the present invention.

Referring to FIG. 22, the electronic device 200 may have a circular shape including a case 201 in circular shape. The electronic device 200 may include a plurality of the electrodes 231 to 234 and a plurality of the load cells 241 to 244. The electronic device 200 may include a plurality of displays respectively provided in different directions or a single display 250. For example, the electronic device 200 may include the single display 250 and be located at a center of the electronic device 200. In this case, when a user steps down from the electronic device 200, the controller 280 may output a measured biometric information to the display 250 located at the center.

The electronic device 200 according to various embodiments of the present invention can send a measured biometric information to another communication-connected device or may enable the measured biometric information to be outputted to a display of another device.

This is described with reference to FIGS. 23 to 25.

Figure 23:
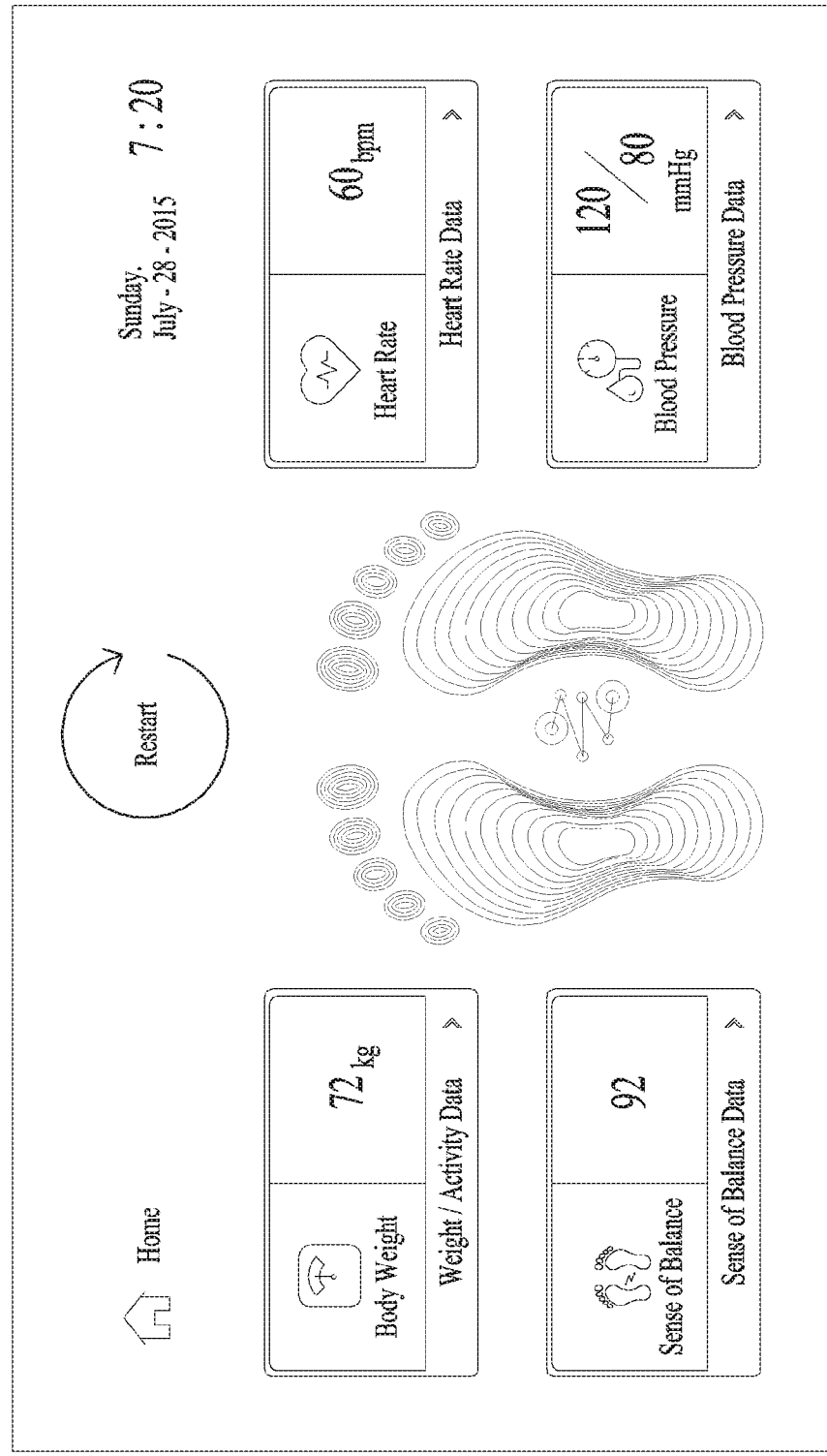
FIGS. 23 to 25 are diagrams for examples of an output screen for biometric information according to various embodiments of the present invention.
Figure 24:
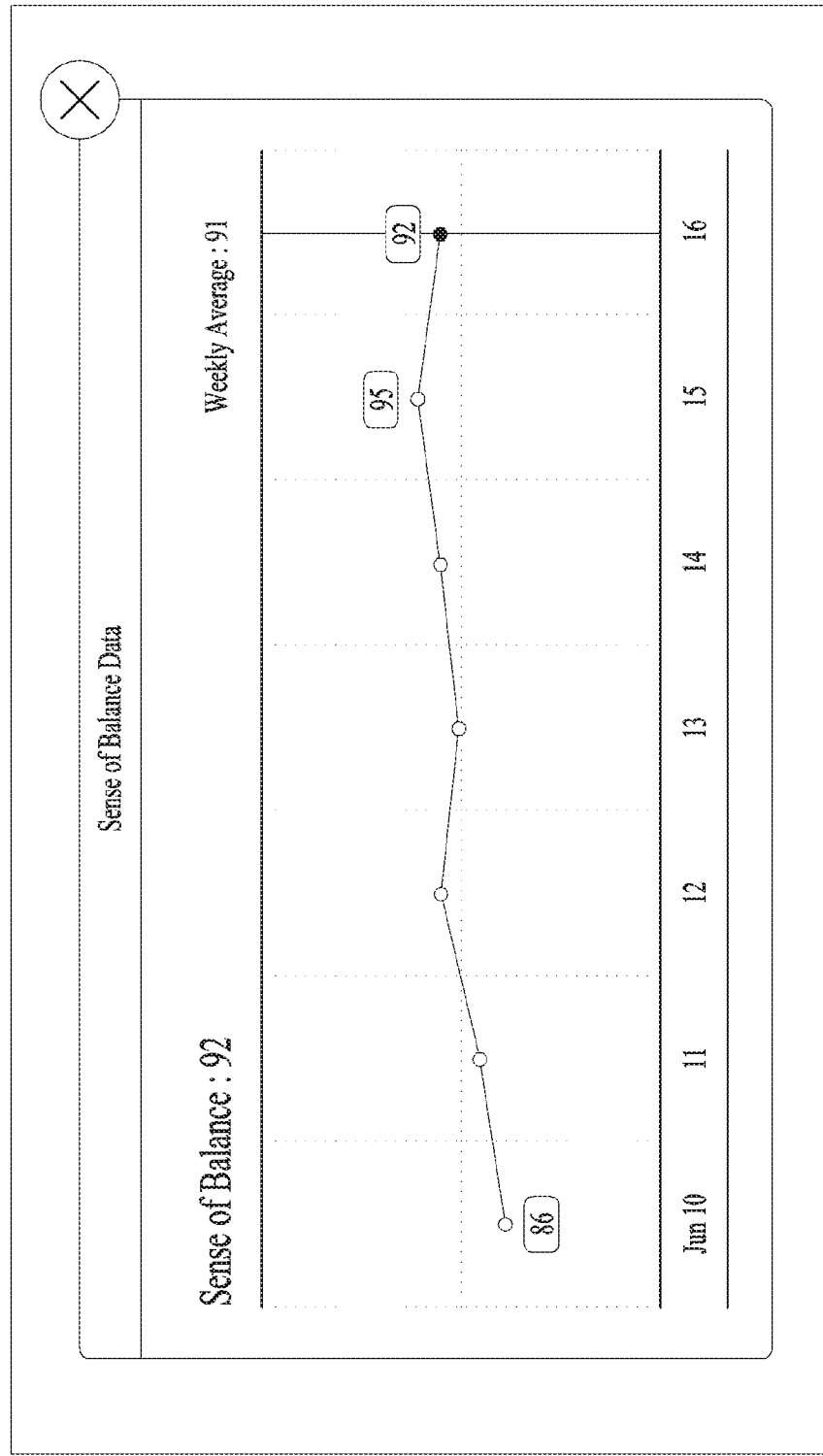
Figure 25:
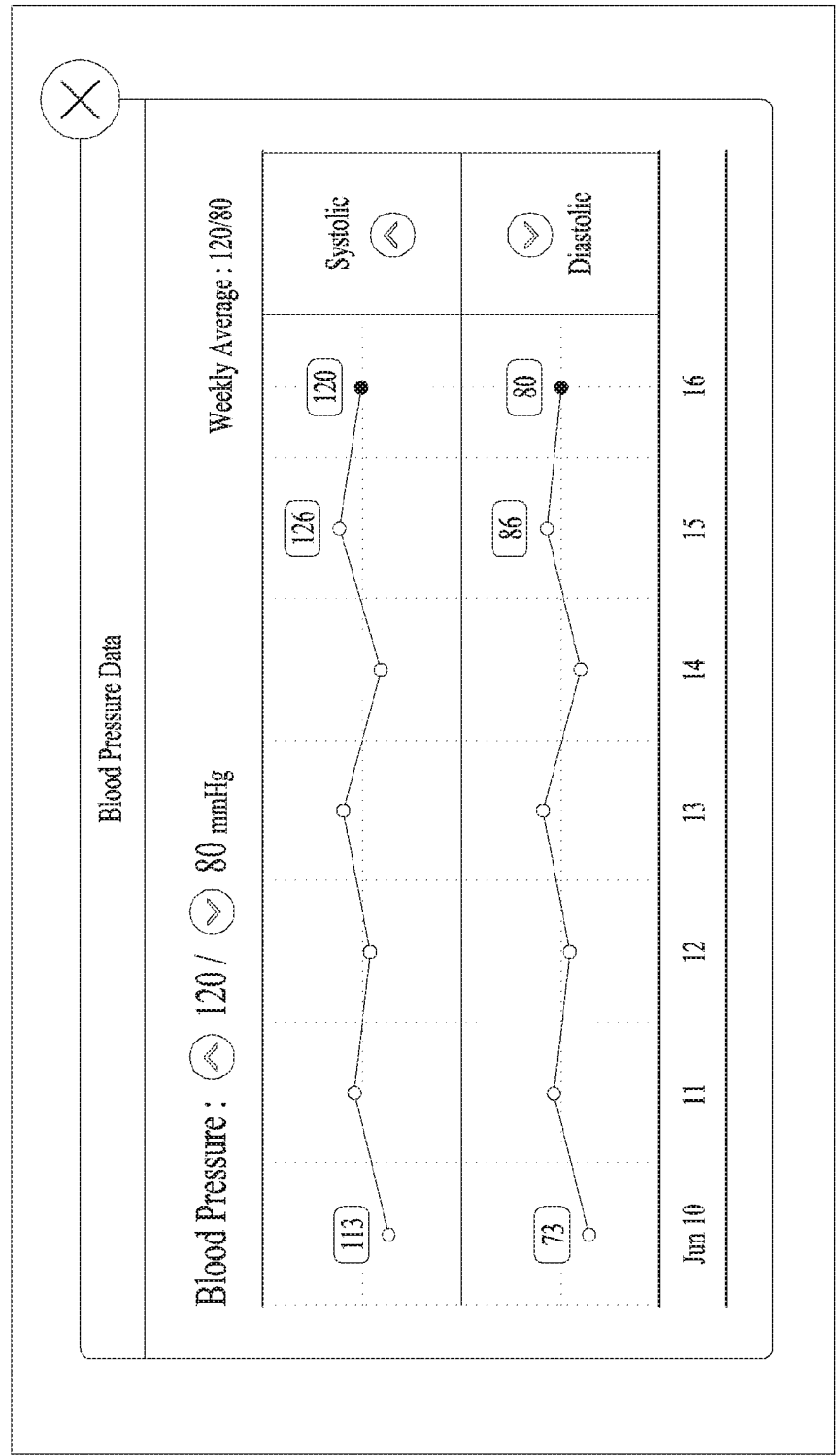

FIGS. 23 to 25 are diagrams for examples of an output screen for biometric information according to various embodiments of the present invention.

Referring to FIG. 23, various biometric informations may be outputted to a screen. For instance, user's weight, heart rate, body balance and blood pressure, which are measured by the electronic device 200, can be outputted to the screen. Herein, the screen for outputting various biometric informations may include the display 250 provided to the electronic device 200 or another display unit 151 of another electronic device 100 communication-connected to the electronic device 200. For example, the screen may include a display of a terminal communication-connected to the electronic device 200 or a video display device connected to the electronic device 200. Meanwhile, if a prescribed biometric information is selected from various biometric informations displayed on the screen, details of the selected biometric information may be outputted to the screen.

Referring to FIG. 24, if the body balance is selected, details of the user's body balance may be outputted to the screen. For instance, user's body balances and fluctuations for a predetermined period and an average body balance for the predetermined period may be outputted to the screen.

Referring to FIG. 25, if the blood pressure is selected, details of the user's blood pressure may be outputted to the screen. For instance, user's blood pressures and fluctuations for a predetermined period and an average blood pressure for the predetermined period may be outputted to the screen.

Thus, the electronic device 200 can output the measured biometric information through various devices as well as through the display 250 of the electronic device.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. An electronic device, comprising:
a plurality of displays respectively located in different directions;
a sensor comprising a plurality of load cells, each of the plurality of load cells configured to measure a load of a user;
four electrodes configured to be in contact with a body part of the user to enable a current to flow through the user's body part; and
a controller operably coupled to the plurality of displays, the sensor, and the four electrodes and configured to:
recognize two electrodes initially in contact with the user's body part among the four electrodes as a first pair of electrodes;
recognize the rest of the four electrodes in contact with the user's body part, in pairs of two, as a second pair of electrodes;
measure a current flowing between the recognized first and second pairs of electrodes;
determine biometric information of the user based on the measured current and loads;
determine a weight center of the user based on the load sensed by each of the plurality of load cells; and
cause one of the plurality of displays to display the determined biometric information,
wherein a direction of the one of the plurality of displays corresponds with the determined weight center.

2. The electronic device of claim 1, wherein the controller is further configured to:
measure the current flowing from at least one electrode included in the first pair of electrodes to at least one electrode included in the second pair of electrodes via the user's body part; and
measure a bioelectrical impedance corresponding to the user based on the measured current.

3. The electronic device of claim 1, wherein the controller is further configured to:
determine a shift of the weight center of the user; and
perform an operation corresponding to the shifted weight center.

4. The electronic device of claim 3, wherein the controller is further configured to:

determine a second weight center corresponding to the shifted weight center with reference to a first weight center corresponding to the weight center initially recognized for the user; and cause another one of the plurality of displays to display information corresponding to the second weight center, wherein a direction of the other one of the plurality of displays corresponds with the second weight center.

5. The electronic device of claim 4, wherein the controller is further configured to cause the other one of the plurality of displays to:

display first biometric information; and display second biometric information when the shifted second weight center is in a left direction relative to the one of the plurality of displays corresponding with the first weight center; and display third biometric information when the shifted second weight center is in a right direction relative to the one of the plurality of displays corresponding with the first weight center.

6. The electronic device of claim 4, wherein the controller is further configured to:

cause the other one of the plurality of displays to display a confirmation request message;

input a confirmation input for the confirmation request message when the shifted second weight center is in the left direction relative to the one of the plurality of displays corresponding with the first weight center; and input a cancellation input for the confirmation request message when the shifted second weight center is in a right direction relative to the one of the plurality of displays corresponding with the first weight center.

7. The electronic device of claim 1, wherein the biometric information comprises at least one of blood pressure, body fat, muscle mass, fat mass, body fluid, bone mass, BMI (body mass index), metabolic age, body balance, or basal metabolic rate of the user.

8. The electronic device of claim 1, wherein a number of the plurality of displays is four.

9. The electronic device of claim 8, wherein a number of the plurality of load cells is four.

10. The electronic device of claim 8, wherein each of the plurality of displays is located at a respectively corresponding one of four sides of the electronic device.

11. A method of operating an electronic device comprising a plurality of displays respectively located in different directions, a sensor comprising a plurality of load cells, each of the plurality of load cells configured to measure a load of a user, four electrodes, and a controller operably coupled to the plurality of displays, the sensor, and the four electrodes, the method performed by the controller and comprising:

recognizing two electrodes initially in contact with a body part of the user among the four electrodes as a first pair of electrodes;

in contact with the user's body part, in pairs of two, as a second pair of electrodes;

measuring a current flowing between the recognized first and second pairs of electrodes;

determining biometric information of the user based on the measured current and loads;

determining a weight center of the user based on the load sensed by each of the plurality of the load cells; and causing one of the plurality of displays to display the determined biometric information, wherein a direction of the one of the plurality of displays corresponds with the determined weight center.

* * * * *